(12) United States Patent
Pageat

(10) Patent No.: US 11,020,364 B2
(45) Date of Patent: Jun. 1, 2021

(54) PALMITOLEIC ACID FOR USE IN INHIBITING THE ATTACHMENT OF SEA LICE TO FISH

(71) Applicant: INSTITUT DE RECHERCHE EN SEMIOCHIMIE ET ETHOLOGIE APPLIQUEE, Apt (FR)

(72) Inventor: Patrick Pageat, Apt (FR)

(73) Assignee: INSTITUT DE RECHERCHE EN SEMIOCHIMIE ET ETHOLOGIE APPLIQUEE, Apt (FR)

( * ) Notice: Subject to any disclaimer, the term of this patent is extended or adjusted under 35 U.S.C. 154(b) by 251 days.

(21) Appl. No.: 15/503,143

(22) PCT Filed: Aug. 7, 2015

(86) PCT No.: PCT/IB2015/001887
§ 371 (c)(1),
(2) Date: Feb. 10, 2017

(87) PCT Pub. No.: WO2016/024168
PCT Pub. Date: Feb. 18, 2016

(65) Prior Publication Data
US 2017/0231939 A1     Aug. 17, 2017

Related U.S. Application Data

(60) Provisional application No. 62/036,436, filed on Aug. 12, 2014.

(51) Int. Cl.
*A61K 31/201*     (2006.01)

(52) U.S. Cl.
CPC .................. *A61K 31/201* (2013.01)

(58) Field of Classification Search
CPC .................................. A61K 31/201
See application file for complete search history.

(56) References Cited

U.S. PATENT DOCUMENTS

| | | | | |
|---|---|---|---|---|
| 4,052,425 A | * | 10/1977 | Leonard | C08F 20/64 554/175 |
| 6,982,285 B2 | | 1/2006 | Schmid | 514/595 |
| 7,879,809 B2 | | 2/2011 | Dick et al. | 514/28 |
| 2006/0210611 A1 | * | 9/2006 | Immig | A23K 40/00 424/442 |
| 2009/0130149 A1 | | 5/2009 | Raa et al. | 424/265.1 |
| 2010/0022649 A1 | * | 1/2010 | Laguna Granja | A61K 36/889 514/560 |

FOREIGN PATENT DOCUMENTS

| | | | | |
|---|---|---|---|---|
| WO | WO 01/07047 A2 | 2/2001 | | A61K 31/44 |
| WO | WO 2010/077152 A1 | 7/2010 | | A61K 31/122 |
| WO | WO 2011/101367 A1 | 8/2011 | | A61K 36/61 |
| WO | WO 2011/135384 A1 | 11/2011 | | A01N 61/00 |
| WO | WO-2011135384 A1 | * 11/2011 | | A01N 25/002 |
| WO | WO 2014/020339 A1 | 2/2014 | | A01N 35/04 |

OTHER PUBLICATIONS

International Search Report from corresponding International Patent Application No. PCT/IB15/01887, dated Dec. 9, 2015.
Written Opinion of the International Searching Authority from corresponding International Patent Application No. PCT/IB15/01887, dated Dec. 9, 2015.
Saify et al., "A Study on Fatty Acid Composition of Fish Oil From Two Marine Fish, *Eusphyra blochii* and *Carcharhinus bleekeri*," Pakistan Journal of Pharmaceutical Science, vol. 13, No. 2, Jul. 1, 2000, pp. 5-12.

* cited by examiner

*Primary Examiner* — Kevin E Weddington
(74) *Attorney, Agent, or Firm* — Kusner & Jaffe

(57) ABSTRACT

A semiochemical composition comprising a sea lice copepodits attachment inhibiting semiochemical comprising a synthesized palmitoleic acid, salts thereof, derivatives thereof, isomers thereof and/or structural analogs thereof and/or mixtures thereof and an acceptable vehicle is described. Also described are methods to treat sea lice comprising administering to fish in need of such treatment a semiochemical composition comprising a sea lice attachment inhibiting semiochemical comprising a synthesized palmitoleic acid, salts thereof, derivatives thereof, isomers thereof and/or structural analogs thereof and/or mixtures thereof and an acceptable vehicle.

13 Claims, 12 Drawing Sheets

Body

Gills

PALMITOLEIC ACID FOR USE IN INHIBITING THE ATTACHMENT OF SEA LICE TO FISH

TECHNICAL FIELD

The present invention relates to a semiochemical composition comprising a sea lice copepodits attachment inhibiting semiochemical comprising a synthesized palmitoleic acid, salts thereof, derivatives thereof, isomers thereof and/or structural analogs thereof and/or mixtures thereof and an acceptable vehicle. It also relates to methods to treat sea lice comprising administering to fish in need of such treatment a semiochemical composition comprising a sea lice attachment inhibiting semiochemical comprising a synthesized palmitoleic acid, salts thereof, derivatives thereof, isomers thereof and/or structural analogs thereof and/or mixtures thereof and an acceptable vehicle.

BACKGROUND OF THE INVENTION

Sea lice are regarded as being one of the most important causes for sanitary and economical loss in fish production (Johnson et al, 2004). In Atlantic salmon (*Salmo salar*) and rainbow trout (*Oncorhynchus mykiss*), *Lepeophtheirus salmonis* and other caligid copepodids, are regarded as a major obstacle to the development of salmonid fish farming, leading the authorities to refrain from the creation of new farms, as long as there is no satisfying treatment (Stewart et al 2004).

*Lepeophtheirus salmonis*, which appears currently as the most common and important species, shows a complex lifecycle including very different lifestages. Among those, the copepodit stage is especially interesting, since this is the infesting stage (Pike and Wadsworth, 1999). As the first larval stages (Nauplius I and II), the copepodite does not have a functional digestive tract, but is using the energy obtained from the catabolism of its adipous tissue. Its lifespan seems to be limited to 2 weeks, during which it must attach on a host via the antennal hooks. The copepodits, as most planktonic organisms, are passively moved by the stream, even if they have the capability to show some speed movements which makes it possible to catch the host and attach on it. Literature reports that the contact with the host is facilitated by a burst swimming response to linear water accelerations (frequency of 3±12 Hz, which lasts for 1±3 s) (Heuch & Karlsen, 1997). This behavior is probably originating in a predator-avoiding strategy observed in free ranging copepodits (Heuch & Karlsen, 1997). The high frequency of first infestation on the fins, may be regarded as another argument supporting the hypothesis that the copepodits are activated by small-scale water movements generated in their proximity (Tully et al, 1993a). Some authors (Anon, 1993) have suggested that there may be an important passive infestation through the gill cavity, the chalimus, after metamorphosis, migrating to the body surface. More recent studies suggest that this theory may result from artifacts during experimental infestations. The low frequency of gill infestations in reports about natural massive infestations, must be regarded as a strong argument against this hypothesis (Tully et al, 1993b and 2002).

After hooking onto the fish, the copepodit seems to use chemosensory information. Antennal chemoreceptors have been described, which may explain that copepodits attaching on inappropriate hosts (non-salmonid fish) detach and return to the stream (Bron 1993).

Different studies have described the role of semiochemicals in the infestive behavior of *Lepeophtheirus*. Before any study made it possible to identify some chemical components, different observations underlined the probability for the involvement of semiochemical information. The antennae of the copepodits carry sensory captors and are also responsible for hooking onto the fish (Bon 1993). As previously described, the copepodits tend to dehook when they attach on a non-salmonid fish, and such discrimination appears to be very probably due to chemical information. Presence of chemical signals, released by the fish skin, is not surprising, since the cutaneous mucus has been proven to include various lipidic compounds, very well known for their participation in chemical communication among various species (Lewis 1970).

But the most significant literature was obtained due to the evidence of the attracting effect of "fish conditioned water", which is obtained by sampling water in which a fish has been swimming (Ingvarsdöttir et al 2002, Bailey & Mordue 2003, Pino-Marambio et al 2007 & 2008). Some precise compounds have been identified and between them the isophorone and 1-octen-3-ol appear to be selectively detected by the antennae. Unfortunately, most of the published data have been obtained concerning adult sea lice, which are not at the infestive lifestages of the parasite.

Some other data suggest that stress influences the vulnerability of salmonids facing sea lice infestation (Tully et al 1993 a & b, MacKinnon 1998, Mustafa & MacKinnon 1999). This stress may be related to various stimuli between which smoltification (Barton et al 1985) and social stress, in species which cannot be regarded as really domesticated, appears to be of major importance (Sloman et al 2001, Gilmour et al 2005). The elevation of plasmatic cortisol may play a role by decreasing the concentration of antibodies and especially the concentration of IgM immunoglobins in the cutaneous mucus (Magnadöttir 1998, Hou et al 1999). These antibodies appear to play a role in the immunity against the infestation, with a probable effect on the attachment of the filament carried by the chalimus larvae (Tully et al 2002).

Fish farming has led to the escape of fish from the farm and integration into wild salmon populations. This has an impact in the wild fish population for transmission of disease and competition for food. Farmed fish have many altered traits compared to their wild counterparts. One such trait is that farmed fish are more aggressive than their wild counterparts (Johnson & Abrahams, 1991). Another trait is that the progeny of farmed fish grow faster than wild fish (Fleming et al 2000). As a consequence of fish farming the number of hosts for salmon lice has multiplied.

There are two types of sea lice, namely *Lepeophtheirus* (*Lepeophtheirus salmonis*) and *Caligus* (*Caligus elongatus*). They are recognized by their brown horse shoe shaped shell. They firmly attach to fish and damage them by eating the scales, cell tissue, blood and mucous membranes. The immune system of fish is weakened leading to secondary infections and the possibility of fish mortality. A salmon smolt that has more than 10 to 15 salmon lice is weakened and is not likely to survive its sojourn in the sea before returning to the river to spawn. Low nonlethal infestations of sea lice can induce stress responses in fish leading to salt imbalance, reduced immunity and greater infection. (Tully et al 2002). Generally twelve to fifteen sea lice can kill a wild salmon. There are basically treatments for salmon lice, one being biological and the other chemical. The use of wrasse, which are marine fish of the family Labridae (order Perciformes), can pick off and eat the external parasites of salmon lice is a biological solution. Thus goldskinny wrasse,

*Ctenolabrus*, ballam wrasse, *Labrus bergylta* Ascanius, corking wrasse, *Symphodus meliops* (L.), rock cook, *Centrolabrus exoleus* (L.), cuckoo wrasse, *Labrus bimaculatus* L and scale-rayed wrasse *Acantholabrus palloni* are used for this purpose in the aquaculture industry.

Chemical solutions involve the use of either delousing baths or medicated pellets to be used in fish feed. Bath treatments that are used against salmon lice include organophosphates such as dichlorvos, trichlorfon and azamethiphos; pyrethoids such as cypermethrin and deltamethrin, pyrethrum extract and hydrogen peroxide. Feed treatments include avermectins such as emamectin benzoate, diflubenzuron, teflubenzuron, cypermethrin, cis-cypermethrin and ivermectin. Generally the addition of SLICE (emamectin benzoate) lasts for eight weeks.

However, resistance to the bath and fish feed treatments become apparent overtime leading to ineffective treatment, toxicity to non-target organisms, are stressful to fish and are expensive. In many cases withdrawal periods of the treatment are required and very often re-infestation occurs and especially from farmed salmon where regular parasite treatments places a constant pressure on resistance development.

U.S. Pat. No. 7,879,809 describes the use of spinosyn or a physiologically acceptable derivative or salt for controlling ectoparasite infestation in aquaculture raised fish. Spinosyn is known to be a broad range organic insecticide.

U.S. Pat. No. 6,982,285 describes an injection solution having as an active ingredient1-[4-chloro-3-(3-chloro-5-trifluoromethyl-2-pyridyloxy)phenyl]-3-(2,6-difluoro-benzoly urea) to control fish parasites.

Although pharmaceuticals and chemicals to treat fish parasites such as sea lice are known in the art, they are often environmentally unfriendly. Resistance occurs in many cases leading to lack of efficacy of the treatment and elevated mortality in salmon and other farmed fish. Thus, there is a need for other solutions to solve sea lice infestation.

Semiochemicals are chemicals emitted by a plant or an animal that evoke a behavioral or physiological response in another organism. When the semiochemical affects an individual of the same species, it is called a pheromone. When the semiochemical affects an individual of a different species, it is called an allelochemical.

Those chemical signals that participate in interspecific communications are grouped under the general category of allelochemical signals. The allelochemical signals are generally divided into two subgroups and their function affects the relationship between the emitter of the signal and the receiver of the message. When there is a chemical signal that is emitted, that in relation to the favorable emitter, the sub grouping is known as an allomone. By definition, an allomone is a hormone or substance produced by one species that has an effect upon another species, especially so as to benefit the emitting species. For example, attractive allomones emitted by certain flowers can attract various insects that can pollinate these flowers.

In contrast, when the chemical signal emitted is in relation favorable to the receiver the sub grouping is known as a kairomone. A kairomone, by definition, is a pheromone or substance that can attract other species and sometimes even natural enemies. The kairomones are sometimes implicated in locating a particular host by a parasite. For example, lactic acid that is emitted by human skin is a kairomone known for a number of Culicidae. Allomones and kairomones are natural substances that degrade causing no harm to the end user. These chemicals also do not cause immunity and are safe.

Hence there is a need in the art to provide a composition and a method to inhibit sea lice from attaching to fish which is environmentally friendly, can be easily administered and is effective without harming or stressing the fish or affecting the water environment.

This need and other objects are achieved by the present invention as evidenced by the summary of the invention, description of the preferred embodiments and the claims.

SUMMARY OF THE INVENTION

The present invention relates to a semiochemical composition comprising a sea lice copepodits attachment inhibiting semiochemical comprising a synthesized palmitoleic acid, salts thereof, derivatives thereof, isomers thereof and/or structural analogs thereof that maintain their semiochemical capabilities to detach sea lice from fish and/or mixtures thereof that detaches sea lice from fish and an acceptable vehicle.

In another aspect a semiochemical composition comprising a sea lice copepodits attachment inhibiting semiochemical comprising from about 0.1 ppm to about 10 ppm of a synthesized palmitoleic acid, salts thereof, derivatives thereof, isomers thereof and/or structural analogs that maintain their semiochemical capabilities to detach sea lice from fish and/or mixtures thereof and a nontoxic filler and/or enhancer composition and an acceptable vehicle.

In another aspect a semiochemical composition comprising a sea lice copepodits attachment inhibiting semiochemical comprising from about 0.6 ppm to about 6 ppm of a synthesized palmitoleic acid, salts thereof, derivatives thereof, isomers thereof and/or structural analogs thereof that maintain their semiochemical capabilities to detach sea lice from fish and/or mixtures thereof and an acceptable vehicle.

The acceptable vehicle, as described herein, is a pharmaceutically acceptable vehicle or a veterinarian acceptable vehicle.

The sea lice copepodits attachment inhibiting semiochemical composition comprising a synthesized palmitoleic acid, as described herein, can further comprise a nontoxic filler or an enhancer composition. The nontoxic filler is selected from the group of fatty acids, alcohols, amines, squalene, glycerol and mixtures thereof, while the enhancer composition contains amines and fatty acids from indolic derivatives, esters of these amines and fatty acids, ketones, acetone, alcohols or sterols.

In yet another aspect the sea lice copepodits attachment inhibiting semiochemical composition, as described herein, is an ester, an alcohol, a ketone, an amide, an ether, an aldehyde or a sterol derivative of a synthesized palmitoleic acid, salts thereof, isomers thereof and/or structural analogs thereof that maintain their semiochemical capabilities to detach sea lice from fish and/or mixtures and an acceptable vehicle.

The semiochemical composition can be in the form of powders, tablets, pellets, capsules, granulated, granulated particles, dry flakes or other forms suitable for use. It can also be in the form of a sustained release formulation, placed in micelles, liposomes, nanoparticles, microparticles or microencapsulated. The semiochemical composition can also be lyophilized.

A solution or solutions containing the composition comprising the sea lice copepodits attachment inhibiting semiochemical comprising a synthesized palmitoleic acid, salts thereof, isomers thereof and/or structural analogs thereof that maintain their semiochemical capabilities and/or mixtures is another aspect of the invention. The solutions can be formulated with an acceptable vehicle such as a pharmaceutically acceptable vehicle or a pharmaceutically acceptable vehicle. The solutions can also contain a nontoxic filler, as described herein, or an enhancer composition, as described herein.

This solution comprises the sea lice copepodits attachment inhibiting semiochemical compositions from about 0.1 ppm to about 10 ppm of a synthesized palmitoleic acid, salts thereof, isomers thereof and/or structural analogs thereof that maintain their semiochemical capabilities to detach sea lice from fish and/or mixtures is yet another aspect of the invention. This solution can be formulated with an acceptable vehicle such as a pharmaceutically acceptable vehicle or a veterinarian acceptable vehicle. The solutions can also contain a nontoxic filler, as described herein, or an enhancer composition, as described herein.

This solution comprises the sea lice copepodits attachment inhibiting semiochemical composition comprising from about 0.6 ppm to about 6 ppm of a synthesized palmitoleic acid, salts thereof, isomers thereof and/or structural analogs thereof that maintain their semiochemical capabilities and/or mixtures is yet another aspect of the invention. This solution can be formulated with an acceptable vehicle such as a pharmaceutically acceptable vehicle or a veterinarian acceptable vehicle. The solutions can also contain a nontoxic filler, as described herein or an enhancer composition, as described herein.

The solution can be in the form of a spray, an aerosol, an emulsion, a suspension, in the form of drops, can be placed in an under water diffuser or in a slow release matrix. It can be added to the water where the fish reside or placed in the food of the fish. It also can be administered orally or via injection to the fish.

A method to detach sea lice from fish, is yet another aspect of the invention, said method comprising administering to fish a semiochemical composition comprising a sea lice copepodits attachment inhibiting semiochemical comprising a synthesized palmitoleic acid, salts thereof, derivatives thereof, isomers thereof and/or structural analogs thereof that maintain their semiochemical capabilities to detach sea lice from fish and/or mixtures thereof and an acceptable vehicle.

A method to detach sea lice from fish, is yet another aspect of the invention, said method comprising administering to fish a semiochemical composition comprising a sea lice copepodits attachment inhibiting semiochemical comprising 0.1 ppm to 10 ppm of a synthesized palmitoleic acid, salts thereof, derivatives thereof, isomers thereof and/or structural analogs thereof that maintain their semiochemical capabilities to detach sea lice from fish and mixtures thereof and an acceptable vehicle.

A method to detach sea lice from fish, is yet another aspect of the invention, said method comprising administering to fish a semiochemical composition comprising a sea lice copepodits attachment inhibiting semiochemical comprising 0.6 ppm to 6 ppm of a synthesized palmitoleic acid, salts thereof, derivatives thereof, isomers thereof and/or structural analogs thereof that maintain their semiochemical capabilities to detach sea lice from fish and mixtures thereof and an acceptable vehicle.

A semiochemical composition comprising a synthesized palmitoleic acid, salts thereof, derivatives thereof, isomers thereof and/or structural analogs thereof that maintain their semiochemical capabilities to detach sea lice from fish and mixtures thereof and an acceptable vehicle for use in inhibiting attachment of sea lice to fish is another aspect of the invention.

A semiochemical composition comprising about 0.1 ppm to about 10 ppm of a synthesized palmitoleic acid, salts thereof, derivatives thereof, isomers thereof and/or structural analogs thereof that maintain their semiochemical capabilities to detach sea lice from fish and mixtures thereof and an acceptable vehicle for use in inhibiting attachment of sea lice to fish is another aspect of the invention.

A semiochemical composition comprising about 0.6 ppm to about 6 ppm of a synthesized palmitoleic acid, salts thereof, derivatives thereof, isomers thereof and/or structural analogs thereof that maintain their semiochemical capabilities to detach sea lice from fish and mixtures thereof and an acceptable vehicle for use in inhibiting attachment of sea lice to fish is another aspect of the invention.

DESCRIPTION OF THE PREFERRED EMBODIMENTS

Figure 1:
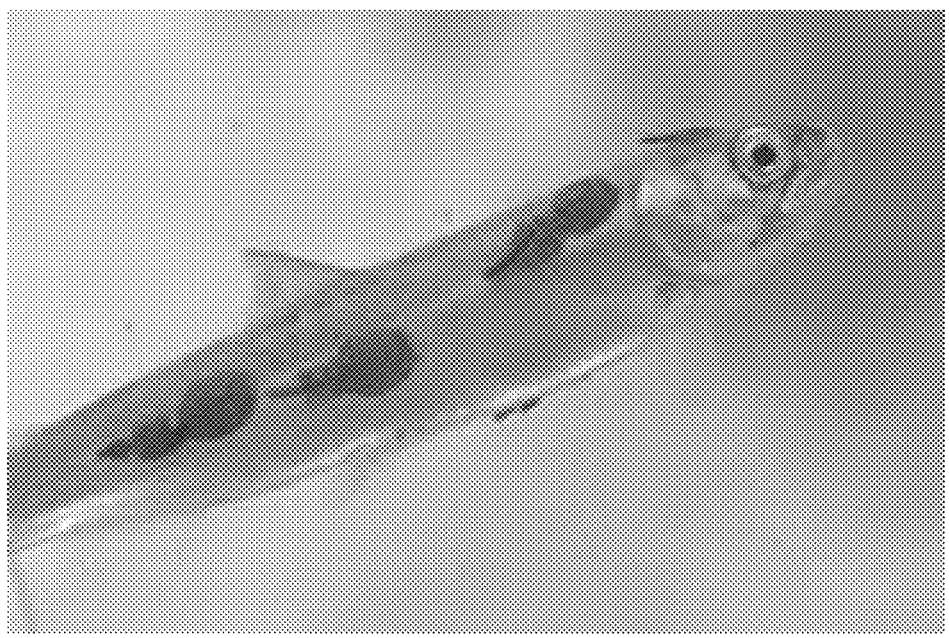
FIG. 1 is a photograph of sea lice on a juvenile salmon.

"Fish" as used herein includes any member of the Phylum Chordata Sub Phylum Vertebrate and Superclasses Agnatha, Chrondrichthyes and Osteichthyes, class: Actinopterygii Order: Salmoniformes or Perciformes or Siluriformes By way of example, but not being restrictive, the following fish species may be mentioned as encompassed by the present invention catfish, carp, trout, salmon, sea bass, sea bream, whitefish, char, grayling and perch.

Amongst catfish that are encompassed by the present invention include channel catfish, blue catfish, flathead catfish, yellow catfish and the like. Carps include common carp, silver carp, grass carp and the like. Trout include Green Back Cutthroat trout, Rio Grand Cutthroat trout, Snake River Cutthroat trout, Brown trout, Brook trout, Hybrid Cut-Bow trout, Rainbow trout, Palomino rainbow trout and the like. Salmon includes Chinook, Coho, Sockeye, Chum, Pink salmon, Atlantic salmon, Steelhead salmon and the like. Sea Bass include Bank sea bass, Chilean sea bass, Black sea bass, Rock sea bass, spotted sea bass and the like. Sea breams include Black sea breams, Gilt-head sea bream and Red sea breams. Whitefish include common whitefish, lake whitefish, Atlantic whitefish, round whitefish, Mountain whitefish, Inconnu, Ocean whitefish, Beluga sturgeon, Caspian whitefish, white steenbras and the like. Char include Dolly Varden char, Atlantic char, Wisconsin Ivory char and the like. Grayling includes European grayling, Arctic grayling and the like. Perch include climbing perch, European perch, Balkhash perch, Yellow perch, Golden perch, Silver perch, Spangled perch, White perch and the like.

By "stress in fish" is meant any physical, chemical or mental discomfort that results in the release of stress-related hormones or in specific physiological responses. Stress causes bodily reactions such as increase in heart rate, blood pressure, increased blood sugar and a release in cortisol levels. It encompasses a rise in cortisol levels to over 100 ng/ml. Enhanced cortisol levels can result in myocardial remodeling in salmonid fish (Johansen et al The Journal of Experimental Biology (2011) 214, 1313-1321). There are different types of stress in fish which include confinement stress handling stress, sorting stress, grading stress and transportation stress. Stress may contribute to decreased resistance in fish leading to the spread of disease and parasite infection. It also has an effect on the feeding behavior, growth and competitive ability of the fish (Gregory et al Physiological and Biochemical Zoology (1999) 72(3) 286-295).

"Aquaculture" as defined herein means the science, art and business of cultivating fish under controlled conditions.

By "active principle" is meant a molecule that confers its therapeutic properties as a sea lice copepodits attachment inhibiting semiochemical comprising synthesized palmitoleic acid, salts thereof, derivatives thereof, isomers thereof and/or structural analogs thereof that maintain their semiochemical capabilities and mixtures thereof.

As used herein the term "sea lice" encompasses any copepod within the order Siphonostomatoida family Caligidae including the genera *Lepeophtheirus* and *Caligus*. Examples include *Lepeophtheirus salmonis, Lepeophtheirus pectoralis, Lepeophtheirus thompsoni, Lepeophtheirus europaensis, Caligus elongatus, Caligus orientalis, Caligus teres, Caligus rogercresseyi, Caligus punctatus, Caligus epidemicus, Caligus clemensi* and the like. Sea lice are found in different waters. Thus for example, *L. salmonis* affects Atlantic salmon in the colder waters of the Northern hemisphere. It also infects salmonids in Japan. *C. orientalis* is also found on rainbow trout in Japan. *C. elongatus* is the most common species in British waters, *C. teres* and *C. rogercresseyi* in Chile, *C. epidemicus, C. punctatus* and *C. orientalis* in Asia and *L. pectoralis* occurs in the north-east Atlantic Ocean, Baltic Sea and White Sea. *C. elongatus* in the Southern hemisphere and especially in Australia.

"Copepodits" as used herein means any of various very small crustaceans of the subclass Copepoda, having an elongated body and a forked tail. Unlike most crustaceans, copepods lack a carapace over the back and do not have compound eyes. They are abundant in both salt and fresh water and are an important food source for many water animals. Copepods include water fleas.

As used herein, the term "cop" is an abbreviation for "copepodites."

As used herein "semiochemical" means a chemical emitted by a plant or an animal that evokes a behavioral or physiological response in another organism. When the semiochemical affects an individual of the same species, it is called a pheromone. When the semiochemical affects an individual of a different species, it is called an allelochemical.

By "allomone" is meant a semiochemical that is produced by one organism to induce a response in an organism of another species. It produces a response favorable to the emitter. For example, some plants produce allomones that repel insects and keep them from feeding.

A chemical messenger emitted by organisms of one species that benefits or affects organisms of another species, as used herein, are "kairomones." An example of a kairomone is a flower scent that attracts or repels animal species.

"Palmitoleic acid" as used herein includes cis-9-hexadecenoic acid or trans-9-hexadecenoic acid and has the molecular formula of $C_{16}H_{30}O_2$. Palmitoleic acid is also known as zoomaric acid, palmitolinoleic acid, (9Z)-hexadecenoic acid, (Z)-hexadec-9-enoic acid, (9Z)-hexadec-9-enoic acid, cis-delta(9)-hexdecenoic acid, 16:1 n-7 or $16:1^{\Delta 9}$.

By "synthesized" is meant that palmitoleic acid is produced chemically or enzymatically and not isolated from nature.

"Derivatives," as used herein, include esters, alcohols, ketones, amides, ethers, aldehydes and sterols of synthesized palmitoleic acid, derivatives thereof, salts thereof, isomers thereof and/or structural analogs thereof, and/or mixtures thereof. These synthesized palmitoleic acid derivatives can replace one or more of the semiochemicals in the composition, as described herein, and have the same effects.

The derivatives of the fatty acids can be synthesized by methods known in the art. For instance, the direct esterification of fatty acids and alcohol catalyzed by an acid catalyst results in a fatty acid ester and water. Fatty aldehydes can be converted to fatty alcohols by hydrogenation. Fatty acid amides can be prepared by reacting an ester of a fatty acid and a lower alcohol with ammonia or mono or dialkyl methyl or ethyl amine under anhydrous conditions and removing the lower alcohol from the reaction.

"Isomers" includes structural isomerism and spatial isomerism. Structural isomers are isomers that have the same component atoms but are arranged differently from each other. An example of a structural isomer is propyl alcohol and isopropyl alcohol. Spatial isomers contain the same atoms linked in an identical manner in the molecule and differing from each other only in the spatial arrangement of the atoms or groups of atoms. Examples of spatial isomers are glucose and dextrose. Examples of palmitoleic acid isomers include 11-cis-hexadecenoic acid and 9-cis,12-cis hexadecanoic acid, and trans-9-hexadecenoic acid.

By "structural analogue" is meant a group of chemical compounds similar in structure to that of another one but differing from it in respect of a certain component. A structural analogue can differ in one or more atoms, functional groups or substructures, which are replaced with other atoms, functional groups of substructures. Examples include 2-methoxy-5-hexadecenoic acid, halogenated palmitoleic acids such as ω-fluropalmitoleic acid, nitrated palmitoleic acid, chlorinated palmitoleic acid, ω-hydroxy decenoic acids and the like.

As used herein the term "mixtures" encompasses the synthesized palmitoleic acid as well as salts thereof, derivatives thereof, isomers thereof and/or structural analogs thereof that maintain the inhibiting attachment of sea lice to fish activity. For example, the mixtures can comprise synthesized palmitoleic acid and isomers of synthesized palmitoleic acid or they can comprise structural analogs of synthesized palmitoleic acid and derivatives of synthesized palmitoleic acid.

The term "solution" is meant a solid or oil that is dispersed in a liquid either by being dissolved or in suspension.

By "acceptable vehicle" is meant any pharmaceutically acceptable vehicle or veterinary vehicle that does not interfere with the activity of the sea lice copepodits attachment inhibiting semiochemical composition comprising synthesized palmitoleic acid salts thereof, isomers thereof and/or structural analogs thereof, and/or mixtures and is not toxic to fish to which it is administered.

By "enhancer composition" is meant an active composition that is species-specific in fish and which can be used to enhance or act synergistically with the basic semiochemical composition, as described herein, to increase the effectiveness in fish of the basic semiochemical composition, as described herein.

By "administering" is meant to apply the sea lice copepodits attachment inhibiting semiochemical composition comprising synthesized palmitoleic acid, as described herein, to the water environment of the fish or to apply the sea lice copepodits attachment inhibiting semiochemical composition comprising synthesized palmitoleic acid, as described herein, to the fish food for ingestion or to apply the sea lice copepodits attachment inhibiting semiochemical composition, as described herein, directly onto or into the fish. Thus oral, injectable, topical administration to fish, as well as placing the semiochemical composition in the environment of fish is contemplated by the present invention.

By "environment" means the fish surroundings.

"Consisting essentially of" means that the sea lice copepodits attachment inhibiting semiochemical composition has the active principle of synthesized palmitoleic acid but can include other compounds that do not affect the semiochemical properties of the active principle.

The present invention relates to a semiochemical composition comprising a sea lice copepodits attachment inhibiting semiochemical comprising synthesized palmitoleic acid, salts thereof, derivatives thereof, isomers thereof and/or structural analogs thereof that maintain their semiochemical capabilities to detach sea lice from fish and/or mixtures and an acceptable vehicle.

The semiochemical composition, as described herein, comprising a sea lice copepodits attachment inhibiting semiochemical comprise from about 0.1 ppm to about 10 ppm or between about 0.6 ppm to about 6 ppm or between about 1 ppm to about 5 ppm or between about 0.05 ppm to about 20 ppm of a synthesized palmitoleic acid, salts thereof, derivatives thereof, isomers thereof and/or structural analogs that maintain their semiochemical capabilities to detach sea lice from fish and/or mixtures thereof and an acceptable vehicle.

In another aspect a semiochemical composition comprising a sea lice copepodits attachment inhibiting semiochemical comprising between about 0.1 ppm to about 10 ppm or between about 0.6 ppm to about 6 ppm or between about 1 ppm to about 5 ppm or between about 0.05 ppm to about 20 ppm of salts of a synthesized palmitoleic acid, derivatives of a synthesized palmitoleic acid, isomers of a synthesized palmitoleic acid and/or structural analogs of a synthesized palmitoleic acid that maintain their semiochemical capabilities to detach sea lice from fish and/or mixtures thereof and a nontoxic filler or enhancer composition and an acceptable vehicle.

In another aspect a composition or compositions comprising a sea lice copepodits attachment inhibiting semiochemical comprising between about 0.6 ppm to about 6 ppm of a synthesized palmitoleic acid or salts thereof, derivatives thereof, isomers thereof and/or structural analogs thereof that maintain their semiochemical capabilities to detach sea lice from fish and/or mixtures thereof and an acceptable vehicle.

The acceptable vehicle is a pharmaceutically acceptable vehicle or a veterinarian acceptable vehicle. It includes solvents, dispersion media, absorption delaying agents and the like. These pharmaceutically acceptable vehicles are described in Remington's Pharmaceutical Sciences 21$^{st}$ edition 2005. An acceptable vehicle can be, for example, glycol ethers or physiological saline. The acceptable vehicle will vary with the way the semiochemical composition is formulated. It can be added to the sea lice copepodits attachment inhibiting semiochemical composition comprising a synthesized palmitoleic acid or salts thereof, derivatives thereof, isomers thereof and/or structural analogs thereof that maintain their semiochemical capabilities to detach sea lice from fish and/or mixtures thereof during formulation.

The pharmaceutically acceptable salts of the semiochemical composition, described herein, include those that are organic or inorganic salts of synthesized palmitoleic acid. These are well known and described in the Physician's Desk Reference, The Merck Index and Goodman and Gilman's The Pharmacological Basis of Therapeutics. The pharmaceutically acceptable salts are, for example, sodium, potassium, ammonium, calcium and magnesium and salts formed with inorganic acids such as hydrochloric acid, hydrobromic acid, phosphoric acid, sulfuric acid and the like or salts formed with organic acids such as oxalic acid, fumaric acid, tartaric acid, malonic acid, acetic acid, citric acid, benzoic acid and the like.

The sea lice copepodits attachment inhibiting semiochemical composition, as described herein, can further comprise a nontoxic filler or an enhancer composition. The nontoxic filler is selected from the group of fatty acids, alcohols, amines, squalene, glycerol and mixtures thereof, while the enhancer composition contains amines and fatty acids from indolic derivatives, esters of these amines and fatty acids, ketones, acetone, alcohols or sterols.

In yet another aspect the sea lice copepodits attachment inhibiting semiochemical composition, as described herein, is an ester, an alcohol, a ketone, an amide, an ether, an aldehyde or a sterol derivative of a synthesized palmitoleic acid, salts thereof, isomers thereof and/or structural analogs thereof that maintain their semiochemical capabilities to detach sea lice from fish and/or mixtures thereof.

The sea lice copepodites attachment inhibiting semiochemical composition, as described herein, can be formulated in a chemical carrier provided that the bioactive structure of the synthesized palmitoleic acid, salts thereof, isomers thereof and/or structural analogs thereof that maintain their semiochemical capabilities to detach sea lice from fish and/or mixtures thereof is preserved. Such carrier molecules include crown compounds such as crown ethers, liposomes, nanoparticles, microparticles and carrier proteins.

Any type of liposomes can be used to entrap the semiochemical composition as disclosed herein. Any natural or synthetic phospholipids such as phosphoglycerides and sphingolipids can be used to fabricate the liposomes. Natural phospholipids such as phosphatidylchooline (PC), phosphotidylethanolamine (PE) and phosphotidylserine can be used. Synthetic phospholipids that can be used include dioleoylphosphatidylcholine, dioleoylphosphatidylethanolamine, distearoylphosphatidylcholine and distearoylphosphatidylethanolamine. Cholesterol can be incorporated into the liposome depending upon the application. Cholesterol can be incorporated in a concentration varying from 1:1 or even 2:1 molar ratios of cholesterol to PC.

The liposomes can be unilamellar vesicles or multilamellar vesicles. The liposomes can also be cross-linked.

Liposomes of the present invention can be made by methods known in the art using passive loading techniques or active loading techniques. Examples of mechanical dispersion methods include lipid film hydration methods, micro emulsion methods, sonication, French press methods, membrane extrusion methods, dried reconstituted vesicle methods and freeze thawed liposome methods. Solvent dispersion methods include ethanol injection, ether injection, double emulsion vesicles, reverse phase evaporation vesicles and stable plurilamellar vesicles. The use of detergent such as cholate and Triton X® 100 and removal of the detergent by dialysis, dilution or column chromatography can also be used for liposome preparation.

Nanoparticles can also be used to deliver the semiochemical composition, as described herein. These particles have a size of less than or equal to 100 nm. They can be fabricated from natural materials or derivatives, dendrimers, fullerenes, polymers, silica, albumin, gold, hydrogels and other materials known in the art. Examples of natural materials for fabricating nanoparticles include chitosan, dextran, gelatine, aliginates and starch. The various polymers that can be used in the nanoparticles of the present invention include polylactic acid, poly(cyano) acrylates, polyethylene amine, block copolymers, polycaprolactone and poly(lactic-co-glycolic) acid (PLGA).

The nanoparticles can be coated with various materials such as a dextran coating, an enteric coating, a polymer coating, a gold coating, a polyethyleneglycol (PEG) coating and a carbohydrate coating.

The nanoparticles can be made using different methods such as attrition, pyrolysis, using thermal plasma methods, gas-phase techniques, multiple emulsion-solvent evaporation methods, gas-flow focusing, electrospray, fluidic nano-precipitation methods, emulsion diffusion-evaporation methods, modified phase inversion/solvent diffusion methods, or sol-gel methods. These methods are described in the literature and known to those skilled in the art.

Microparticles are particles that have a size between 0.1 to 100 μM. They can be fabricated of natural or synthetic polymers using materials similar to those of nanoparticles. Thus, cellulose, starch, lysophosphatidylcholine, poly(lactic acid), phosphorylcholine, poly(DL-lactide-co-glycolide), alginate-spermine, polyamino acids, polyphosphazenes, albumin, dextran, Eudragit S 100, Eudragit L 100, gelatine and 3-(triethoxysilyl)propyl-terminated polydimethylsiloxane are some of the materials that are used to make microparticles. Microparticles of the present invention can also be grafted with other materials. As examples, starch microparticles grafted with polymethyl methacrylate or polyacrylate or silicone-grafted starch microparticles.

Microparticles can also be coated using the same coatings as those described above for nanoparticles; i.e., a dextran coating, an enteric coating, a polymer coating, a gold coating, a Eudragit S 100 coating, a PEG coating and a carbohydrate coating.

In formulating the microparticles several methods can be used such as spray-drying, emulsion/evaporation, double emulsion/evaporation, salting out, solvent displacement/precipitation, cryopreparation, and oil in oil emulsion/solvent evaporation. These and other methods are described in the literature (see, for example, Kendall et al, Eur. J. Pharm, Sci 37, 284-290 (2009)) and are known in the art.

The semiochemical composition, as described herein, can also be in the form of powders, tablets, pellets, capsules, granulated, granular particles, dry flakes or other forms suitable for use. It can also be in the form of a sustained release formulation, placed in micelles or microencapsulated. The semiochemical composition can also be lyophilized.

In one embodiment the semiochemical composition, as described herein, is formulated in a nontoxic water dispersible tablet using chemical formulations of polymers known in the art such as Eudragit, ethyl cellulose, microcrystalline cellulose, talc and magnesium stearate. The polymers are mixed with the semiochemical composition and then compressed using a tableting machine. The size of the tablet may vary depending on the size of the area and number of fish to be treated.

Additional carriers that can be added to the formulation include glucose, lactose, mannose, gum acacia, gelatin, mannitol, starch paste, magnesium trisilicate, talc, corn starch, keratin, colloidal silica, potato starch, urea, short-chain fatty acids, medium chain length triglycerides, dextrans, oligofructans and other carriers suitable for use in manufacturing preparations, in solid, semisolid, or liquid form. In addition, auxiliary stabilizing, thickening or coloring agents can be used, for example as stabilizing and drying agents, such as triulose.

The semiochemical compositions, as described herein, can be diluted in various solutions, as set forth below, and can be used in various liquid forms.

A solution containing a sea lice copepodits attachment inhibiting semiochemical composition comprising a synthesized palmitoleic acid or salts thereof, derivatives thereof, isomers thereof and/or structural analogs thereof that maintain their semiochemical capabilities to detach sea lice from fish and/or mixtures thereof is yet another aspect of the invention.

In another aspect a solution containing a sea lice copepodits attachment inhibiting semiochemical composition comprising a synthesized palmitoleic acid or salts thereof, derivatives thereof, isomers thereof and/or structural analogs thereof that maintain their semiochemical capabilities to detach sea lice from fish and/or mixtures thereof and a nontoxic filler or enhancer composition forms part of the present invention.

The solution can comprise between about 0.1 ppm to about 10 ppm or between about 0.6 ppm to about 6 ppm or between about 1 ppm to about 5 ppm or between about 0.05 ppm to about 20 ppm of a synthesized palmitoleic acid or salts thereof, derivatives thereof, isomers thereof, and/or structural analogs thereof that maintain their semiochemical capabilities to detach sea lice from fish and/or mixtures thereof. Nontoxic fillers or enhancer compositions can be added to the solution.

In another aspect the solution comprising a sea lice copepodits attachment inhibiting semiochemical comprises between about 0.6 ppm to about 6 ppm of a synthesized palmitoleic acid or salts thereof, derivatives thereof, isomers thereof and/or structural analogs thereof that maintain their semiochemical capabilities to detach sea lice from fish and/or mixtures thereof.

The solution can be fabricated by adding a solvent to the synthesized palmitoleic acid or salts thereof, derivatives thereof, isomers thereof and/or structural analogs thereof that maintain their semiochemical capabilities and/or mixtures thereof. Examples of solvents include alkaline solutions, ethyl alcohol, ethanol, ethyl acetate, dimethylformamide, dimethylsulfoxide, physiological saline and the like.

The solution can be in the form of a spray, an aerosol, an under water diffuser, a slow release matrix, can be an injectable and in the form of drops. It can be added to the water as a bath or placed in the food of the fish or applied to the fish or injected into the fish. Thus, oral, topical and injectable treatments are encompassed by the present invention. Also encompassed by the invention is placing the semiochemical composition, as described herein, in the environment of fish.

A fish attractant such as cheese, kernel corn, salt shrimp, crawfish and the like can be added to the composition or the solution as described herein.

A method to detach sea lice from fish, is yet another aspect of the invention, said method comprising administering to fish a semiochemical composition or semiochemical solution comprising a sea lice copepodits attachment inhibiting semiochemical comprising a synthesized palmitoleic acid, salts thereof, derivatives thereof, isomers thereof and/or structural analogs thereof that maintain their semiochemical capabilities to detach sea lice from fish and/or mixtures thereof and an acceptable vehicle.

A method to detach sea lice from fish, is yet another aspect of the invention, said method comprising administering to fish a semiochemical composition or a semiochemical solution comprising a sea lice copepodits attachment inhibiting semiochemical comprising a synthesized palmitoleic acid, salts thereof, derivatives thereof, isomers thereof and/or structural analogs thereof that maintain their semiochemical capabilities to detach sea lice from fish and/or mixtures thereof and a nontoxic filler or enhancer composition and an acceptable vehicle.

A method to detach sea lice from fish, is yet another aspect of the invention, said method comprising administering to fish a semiochemical composition or semiochemical solution comprising a sea lice copepodits attachment inhibiting semiochemical comprising about 0.1 ppm to about 10 ppm or about 0.6 ppm to about 6 ppm or about 1 ppm to about 5 ppm or about 0.05 ppm to about 20 ppm of a synthesized palmitoleic acid, salts thereof, derivatives thereof, isomers thereof and/or structural analogs thereof that maintain their semiochemical capabilities to detach sea lice from fish and/or mixtures thereof and an acceptable vehicle. Nontoxic fillers or enhancer compositions can also be added to the composition.

In this method the semiochemical composition or semiochemical solution are administered for a period of 45 minutes to 2 hours or 10 minutes to 5 hours or 20 minutes to 3 hours. The period of time depends on how the semiochemical composition, as described herein, or semiochemical solution, as described herein, are formulated.

A semiochemical composition, as described herein, or semiochemical solution, as described herein, for use in inhibiting attachment of sea lice to fish is another aspect of the invention.

This semiochemical composition or semichemical solution for use in inhibiting attachment of sea lice to fish comprises about 0.1 ppm to about 10 ppm or about 0.6 ppm to about 6 ppm or about 1 ppm to about 5 ppm or about 0.05 ppm to about 20 ppm of a synthesized palmitoleic acid, salts thereof, derivatives thereof, isomers thereof and/or structural analogs thereof that maintain their semiochemical capabilities to detach sea lice from fish and/or mixtures thereof.

The semiochemical compositions and solutions, as described herein contain a fatty acid. Fatty acids are commercially available from various companies in solid form. They can also be synthesized chemically or enzymatically by methods known in the art. However, since it is difficult to solubilize fatty acids, the fatty acid is generally added to the solvent under constant agitation and at a temperature of between about 37° C. to about 38° C. more preferably about 38° C.

Once obtained, the compositions of the present invention can be tested for the efficacy to inhibit sea lice.

The invention will now be illustrated by the following description of examples which, of course, are not limiting in nature. Further characteristics of the invention will become clear from the following observations that are, of course, provided only by way of illustration and do not in any way limit the scope of the invention.

EXAMPLES

Example 1—Chemical Identification of Putative Semiochemicals 60 salmonid fish (36 salmons and 24 rainbow trout) were sampled for both topographic mucus and blood analysis. A complimentary population of 12 salmon were used for full-body mucus sampling, while 12 non salmonid fish belonging to the Gadidae family were also sampled, for the same purpose. The Gadid population comprised the following genus and species:

*Gadus morhua:* 5 fish
*Pollachius virens:* 10 fish
*Pollachius pollachius:* 2 fish
*Melanogrammus aeglefinus:* 1 fish All the samples, including blood samples and blood smears were chemically analyzed. The blood samples were analyzed for proteins, cortisol plasma levels and volatile compounds, while the blood smears were analyzed for the heterophiles to lymphocytes ratio (HLR) and white blood cells. Half the mucus samples were preserved at −18° C. for immunological assessment and protein identification, while the other half was used for the identification of volatile compounds.

The blood smears were stained according to the May-Grünwald-Giemsa method, for white blood cell counting and the calculation of the heterophiles to lymphocytes ratio (HLR) was undertaken. Basically this method involved fixing the blood smears in methanol for 15 minutes, staining with May-Grünwald for 5 minutes, staining in Giemsa for 10 minutes, rinsing in buffer at pH 6.8, dehydrating in acetone twice, clearing in xylene thrice and counting the white blood cells, heterophiles and lymphocytes to a total of 60 cells.

The blood samples were tested for the assessment of cortisol plasma levels using an ELISA test from Enzo®Life Sciences.

Volatile compounds were first extracted by using different solvents for selective hydrosolubility or liposolubility such as dichloromethane. Such extracts were analyzed using GC-GC/MS methods. The chromatograms and their variations were further analyzed.

The only indicator that has been taken in account, until now, was the plasmatic concentration in cortisol. The values that were measured were comparable to the values published in literature. Notwithstanding, some abnormal values were obtained, especially from salmons.

In salmons, there was no significant difference between fish carrying sealice compared to those without parasite. The two groups show a high concentration of plasmatic cortisol of around 100,000 pg/ml, but the two groups of samples were obtained from fish slaughtered immediately before sampling. To the contrary, in rainbow trout, the infested fish have a higher plasmatic cortisol concentration (78,490.55 pg/ml) compared to the non-infested ones (61,408.75 pg/ml).

The absence of difference in salmon, may be related to slaughtering the fish before blood sampling.

The blood and mucus samples were extracted with dichloromethane and were subjected to gas chromatography/mass spectroscopy (GC/MS) using a Turbo Mass spectrometer made by Perkin Elmer. The detection was effectuated on impact using (EI+) at an energy of 70 eV at 180° C. A JW column type DB 5 having a length of 30 m(id=0.25 mm; film of 25 μm at a split of ½o and a split/splitless of 45 seconds was used.

To confirm the structures of certain molecules obtained from the GC/MS analysis positive chemical ionization (CI+) in methane was performed to visualize the molecular peak (Molecular Mass). This method is well known in the art.

The results were analyzed using a data base to obtain the most probable spectrums. Data bases containing such data are well known in the art.

Five possible interesting semiochemicals were identified. These semiochemicals are set forth below.
Putative Allomone from *Pollachius* (PASA: *Pollachius* Anti Sealice Allomone)

This secretion was obtained from pollock (*Pollachius virens*). It is an association of volatile compounds, which are not present in salmonids. This secretion appears interesting because the population of these fish appeared to be abundantly present around the crates where the salmonids are kept. Moreover, despite the consumption of lost salmon food by these wild fish (most of them showed regurgitation of salmon pellets after capture), and presence in their cutaneous mucus of volatile compounds already present in the food and in the salmonids cutaneous mucus, these fish were not attacked by the sealice.
Putative Allomones from Healthy Salmonids (HRSA1 and 2: Healthy Resistant Salmonid Allomone 1 and 2)

In the cutaneous mucus of non infested salmons and rainbow trout, an association of volatile compounds which may help the copepodits to avoid colonizing fish with effective immune systems was found. Moreover, on comparing this association of compounds to the analysis of non infested salmon or trout living with infested fish, it was possible to subdivide this association of compounds in two subgroups, HRSA1 and HRSA2.
Putative Kairomone from Infested Salmonids (VSSK: Vulnerable Salmonid Sealice Kairomone)

In the cutaneous mucus of infested salmon and rainbow trout, an association of volatile compounds which may help the copepodits to select fish with immune systems that were impaired and made them vulnerable to parasites was found. This secretion has to be differentiated from another chemical pattern which increased in the fish carrying sealice.
Putative Sealice Attracting Pheromone (LHSP: *Lepeophtheirus* Host Signalling Pheromone)

This secretion may be emitted by the lice after achieving their development on a host, or it may be a secretion from the fish, induced by the sealice.

For all the oncoming screening tests, the solutions have been blinded and become A, B, D, E, F for the putative allomones, and M, N, P, Q, R, S, for the putative kairomones. These solutions are described in the following examples.

Example 2—Screening of Putative Semiochemicals

Figure 2:
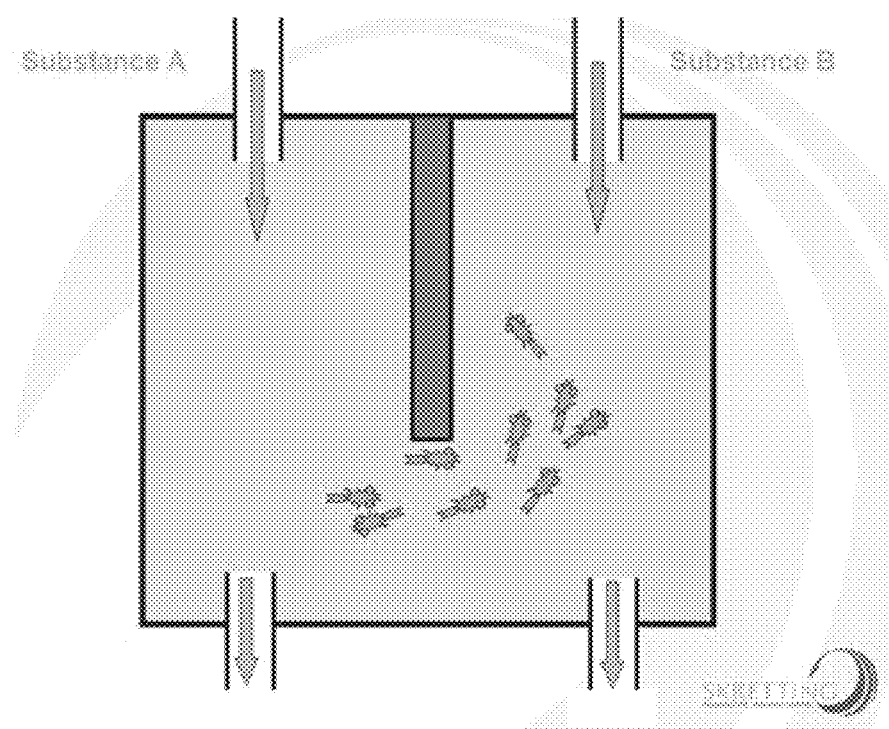
FIG. 2 is a diagram showing the set up of the Smiley Chamber test, which is a test adapted from regular olfactometers.
Figure 3:
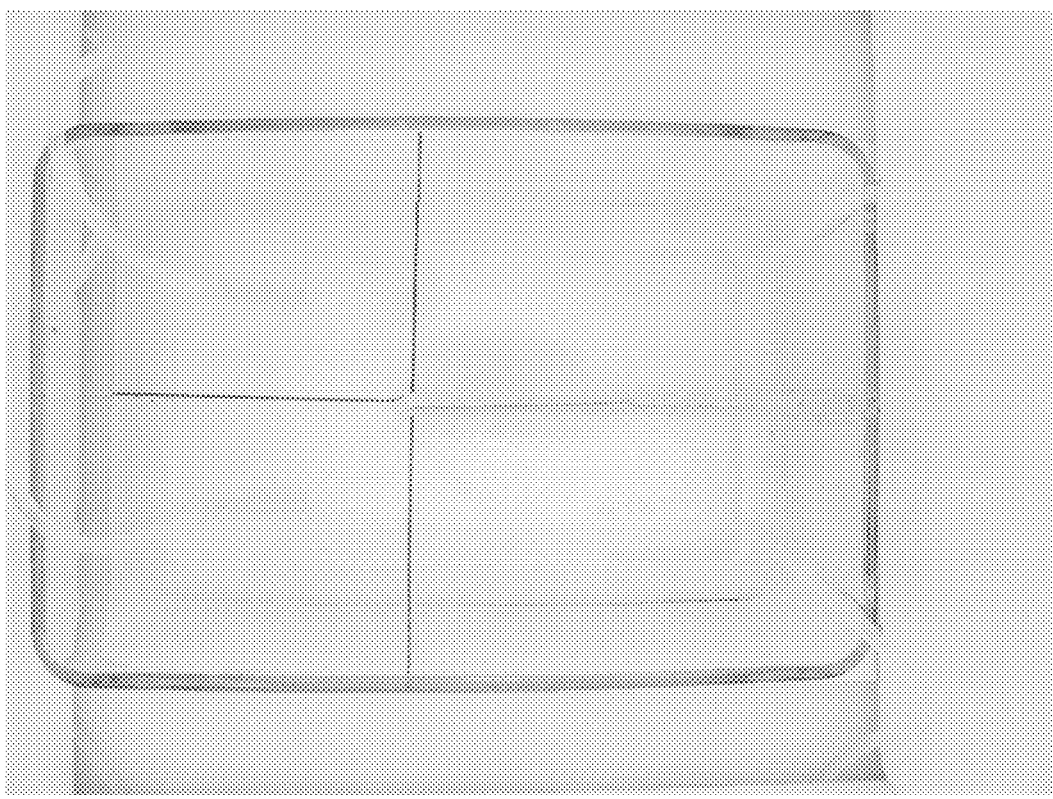
FIG. 3 is a photograph of the original Smiley Chamber test.

The Smiley Chamber test (FIGS. 2 and 3) was used in the assessment of the effects of the putative semiochemicals. This is a test adapted from regular olfactometers.

A set of four 600 ml beakers and four 2 m long tubes for each new semiochemical were separated. The Smiley Chamber and copepodits (cop) cylinder were washed for 30 seconds using running warm fresh water, with detergent for 30 seconds leaving the warm fresh water running, running warm fresh water for an additional 30 seconds, emptying the chamber and spraying 2-propanol in the chamber focusing on the tube holders and the silicone, again running warm fresh water for 30 seconds, running cold water from a water dispenser and finally adding seawater. If necessary, this cleaning protocol was repeated several times.

Three beakers were then filled with 300 to 500 ml of seawater. The remaining beaker was filled with the 6 ppm of the semiochemical. The Smiley Chamber was filled with 300 ml of seawater or just enough to cover the tubes. The pump speed was set at 20 RPM (5.49 ml per minute). The tubes were set equally on the control and test side of the chamber and in the beakers.

To begin the experiment the copepodits cyclinder was placed in the middle of the two outlet tubes and the copepodits were poured into the cylinder while putting pressure on the cylinder via the hand. A check was made to ensure that the copepodits did not escape the cyclinder. A styrofoam wall was placed around the smiley chamber and two lights that were placed above this chamber were turned on. A pump was next turned on and a timer was started. The substance A containing 30% palmitoleic acid, 20% aldehyde C13tridecanal and 50% oleyl alcohol and substance B containing 50% palmitoleic acid and 50% squalene start to enter the chamber after 38 seconds. After 3 minutes and 30 seconds the cylinder with the copepodits was lifted straight up and in slow motion and a camera was placed on the lid. A picture was taken pictures at T0, T3 min, T6 min, T9 min and T10 min. The pump was turned off after 10 minutes ending the experiment. The camera, lid and styrofoam wall were removed and a visual impression of the difference in activity between the control and test side was observed, as well as a visual rough count of the copepodits. The data was analyzed to see whether the reacting copepodits moved in one direction.

The observation of the test with a colorant, showed that after 6 minutes, there was a reflux from one side to the other one, leading to a mixture of the two flows. For that reason, the principle parameter of assessment was the picture at T6 min.

According to the protocol, the putative allomones were tested in competition with conditioned water. This conditioned water consisted of seawater mixed with salmon mucus. To avoid injuring the fish or to pollute the samples with any blood, the mucus was obtained by placing a 500 g salmon in single use plastic bag for 15 seconds. The mucus adhered to the walls of the plastic bag and this mucus was then mixed with 600 ml of seawater. This conditioned water was stored at +4° C. before being used for the test.

Three putative kairomones, E containing 30% palmitoleic acid, 30% oleic acid and 40% squalene; Q containing 30% palmitoleic acid, 30% oleic acid and 40% palmitic acid; and R containing 30% lauric acid, 30% palmitic acid and 40% oleic acid; and 2 putative allomones A containing 30% palmitoleic acid, 20% aldehyde C13tridecanal and 50% oleyl alcohol and B containing 50% palmitoleic acid and 50% squalene were tested. The tests with the conditioned water were used to identify the appropriate concentration required for the tests.

Within the 3 tested kairomones, E containing 30% palmitoleic acid, 30% oleic acid and 40% squalene had been the most effective compound, showing a very visible attracting effect and inducing a clear agitation in the copepodits. Taking into account that a reference attractant isophorone was used as a control the E solution containing 30% palmitoleic acid, 30% oleic acid and 40% squalene showed a very comparable efficacy. Q containing 30% palmitoleic acid, 30% oleic acid and 40% palmitic acid had a versatile, yet not comparable effect.

E containing 30% palmitoleic acid, 30% oleic acid and 40% squalene a putative kairomone obtained from vulnerable salmons, appears to be an interesting kairomone, which efficacy must be confirmed during further testing.

The code E, as described above, corresponded to the putative kairomone group VCCMIS (Volatile Compounds from Cutaneous Mucus of Infested Salmonids).

The allomones A containing 30% palmitoleic acid, 20% aldehyde C13tridecanal and 50% oleyl alcohol and B containing 50% palmitoleic acid and 50% squalene identified in the secretion of non-infested salmon and trout living in infested cages, were tested in competition with the conditioned water. B did not show any visible effect in 4 repeated experiments. To the contrary, A, as described above, showed some interesting effects. 10 duplicated experiments were undertaken of which just 5 provided useful data. A seemed to inhibit the attracting effects of the conditioned water. A, as described above, belonged to the group of putative allomones HRSR (Healthy Resistant Salmonids Release).

Example 3—Screening by Means of a Linear Olfactometer

Figure 4:
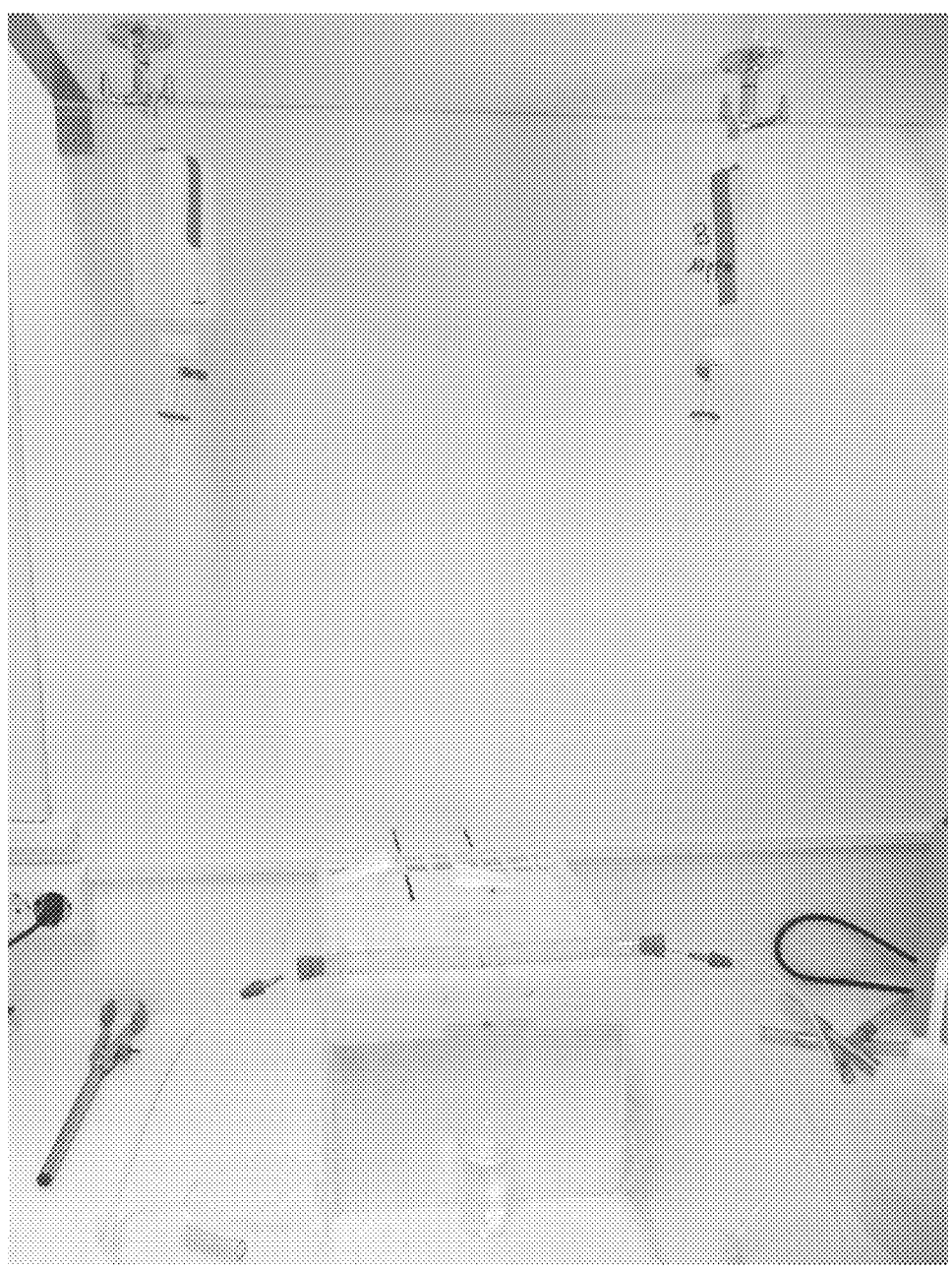
FIG. 4 is a photograph of the olfactory used in the experiments.

The purpose of this trial was to obtain more precise results, with greater precision in the counting of the copepodits. Since the copepodits appear to have a limited mobility, an olfactometer was simplified, using a small device divided in 3 compartments (FIG. 4). This system was first validated regarding the symmetry of the flows carrying the semiochemical (one flow with the reference using ethyl alcohol as the solvent and one flow with the tested mixture). Another improvement in the protocol was the development of a counting method to be certain that the number of copepodits introduced in the olfactometer and counted in each compartment, were precisely counted.

To count the copepodits, they were first fished out of the rearing tank and divided into drops and placed in the wells of an ELISA type plastic plate. A stereoscopic microscope was used to count the copepodits and thus the precise number of copepodits were known and injected in the olfactometer. The linear olfactometer was divided in 3 internal compartments: right and left branch, and central area, plus an external outflow area in which the copepodits were collected in a Petri dish and filtered to count the copepodits.

Figure 5:
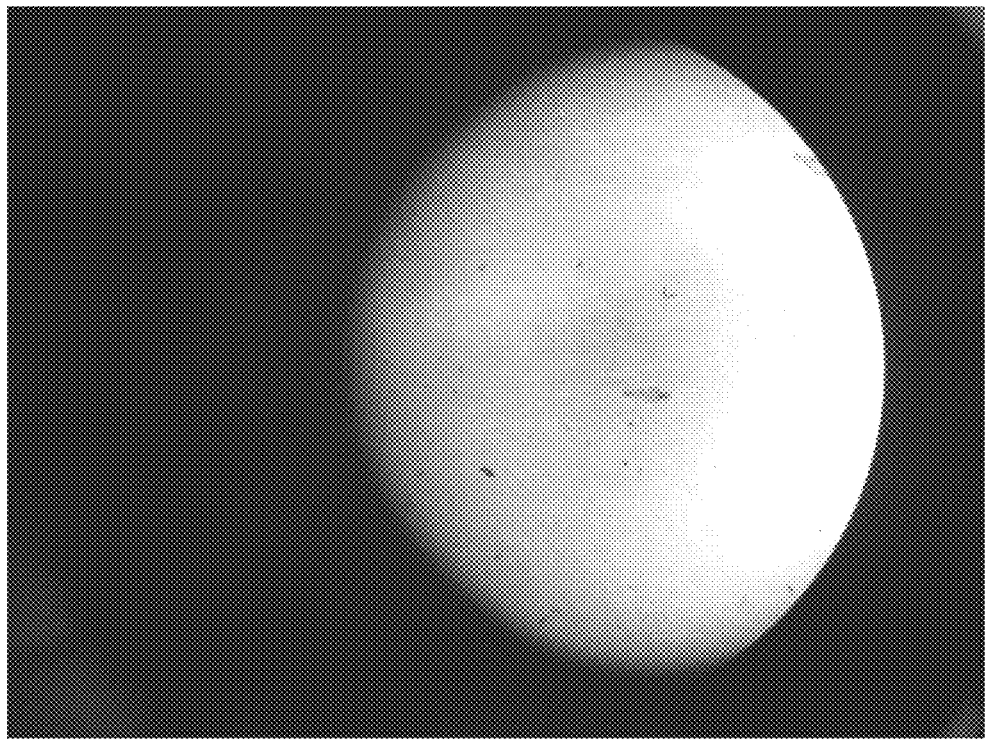
FIG. 5 is a photograph of the copepodits counted after filtering the outflow of the olfactometer.

30 copepodid larvae were introduced in the main branch of the olfactometer, where they faced constant flow (0.84 mVs), at a temperature of 8° C. to 12° C. This flow was divided into 2 sub-flows, each coming from a 250 ml bottle. From one sub-flow, the copepodits received only the solvent of the tested product (ethyl alcohol), from the other sub-flow, they received the putative semiochemical mixture in a concentration of 10 ppm. The test ran for ten (10) minutes. After that time, the flow was stopped and surgical clamps were applied to the tubing on the olfactometer to block the water contained in the 4 areas. This water was examined by a stereoscopic microscope to count the copepodits (FIG. 5).

Three putative allomone mixtures (A, B, D) and four putative kairomones(E, Q, R, S) were tested. The allomone mixtures contained the following compositions:

A: containing 30% palmitoleic acid, 20% aldehyde C13tridecanal and 50% oleyl alcohol.
B: containing 50% palmitoleic acid and 50% squalene.
D: containing 60% oleyl alcohol and 40% squalene.

The Kairomone mixtures contained the following compositions:

E: containing 30% palmitoleic acid, 30% oleic acid and 40% squalene.
Q: containing 30% palmitoleic acid, 30% oleic acid and 40% palmitic acid.
R: containing 30% lauric acid, 30% palmitic acid and 40% oleic acid.
S: containing 40% lauric acid, 40% myristic acid and 20% oleic acid.

The results are shown in the Tables 1 to 6 below. The statistical analysis was calculated by Wilcoxon signed rank.

TABLE 1

Allomone A

| Replica | | Treated Branch | Placebo Branch | M Branch | Waste |
|---|---|---|---|---|---|
| A | 1 | 0 | 1 | 19 | 10 |
|   | 2 | 1 | 2 | 14 | 13 |
|   | 3 | 0 | 4 | 23 | 3 |
|   | 4 | 0 | 2 | 12 | 16 |
|   | 5 | 0 | 3 | 7 | 20 |
|   | 6 | 6 | 0 | 8 | 16 |
|   | 7 | 0 | 1 | 4 | 25 |
|   | 8 | 0 | 3 | 11 | 16 |
|   | 9 | 0 | 4 | 6 | 20 |
|   | 10 | 0 | 3 | 15 | 12 |
|   | Mean | 0.7 | 2.3 | 11.9 | 15.1 |
|   | Median | 0 | 2.5 | 11.5 | 16 |
|   | Standard deviation | 1.888562063 | 1.33749351 | 6.00832755 | 6.10009107 |

Test Treated–placebo p = 0.084

The data was recalculated without the data from number 6 and is set forth in Table 2 below:

TABLE 2

Allomone A without #6

| | Replica | Treated Branch | Placebo Branch | M Branch | Waste |
|---|---|---|---|---|---|
| A without #6 | 1 | 0 | 1 | 19 | 10 |
| | 2 | 1 | 2 | 14 | 13 |
| | 3 | 0 | 4 | 23 | 3 |
| | 4 | 0 | 2 | 12 | 16 |
| | 5 | 0 | 3 | 7 | 20 |
| | 7 | 0 | 1 | 4 | 25 |
| | 8 | 0 | 3 | 11 | 16 |
| | 9 | 0 | 4 | 6 | 20 |
| | 10 | 0 | 3 | 15 | 12 |
| | Mean | 0.111111111 | 2.555555556 | 12.3333333 | 15 |
| | Median | 0 | 3 | 12 | 16 |
| | Standard deviation | 0.333333333 | 1.130388331 | 6.20483682 | 6.46142399 |

Figure 12:
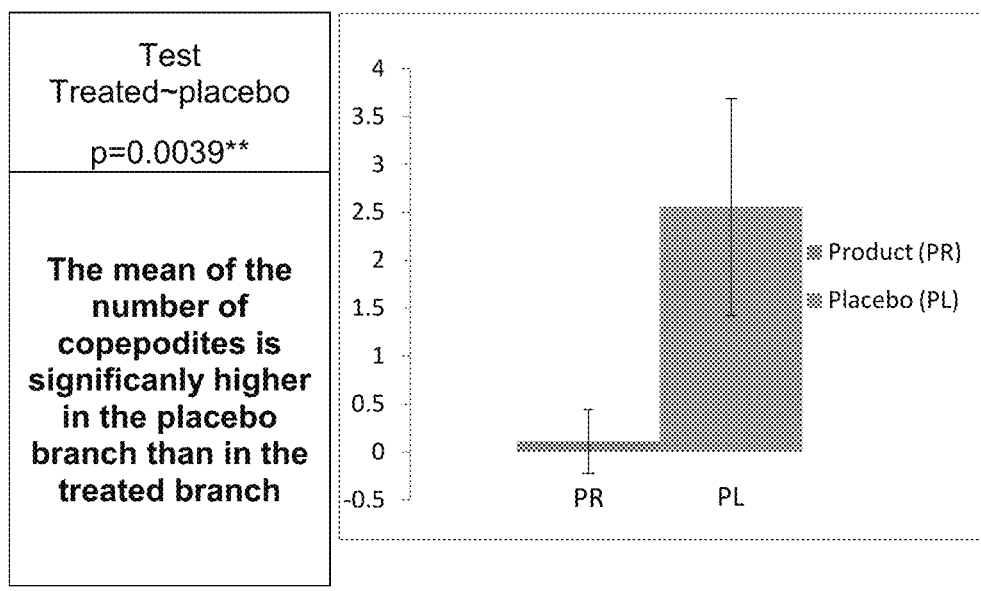
FIG. 12 is a graph showing the mean number of copepodites in the placebo branch versus the treated branch for allomone A.

The graph on FIG. 12 shows that the mean number of copepodites is significantly higher in the placebo branch than in the treated branch for allomone A.

TABLE 3

Kairomone E

| Replica | | Treated Branch | Placebo Branch | M Branch | Waste |
|---|---|---|---|---|---|
| E | 1 | 1 | 2 | 22 | 5 |
|   | 2 | 7 | 0 | 12 | 11 |
|   | 3 | 1 | 9 | 16 | 4 |
|   | 4 | 3 | 3 | 23 | 1 |
|   | 5 | 2 | 5 | 12 | 11 |
|   | 6 | 1 | 1 | 23 | 5 |
|   | 7 | 2 | 5 | 12 | 11 |
|   | 8 | 6 | 4 | 13 | 7 |
| Mean | | 2.875 | 3.625 | 16.625 | 6.875 |
| Median | | 2 | 3.5 | 14.5 | 6 |
| Standard deviation | | 2.356601669 | 2.825268635 | 5.1806646 | 3.79614466 |

Test Treated–placebo p = 0.563

TABLE 4

Kairomone Q

| Replica | | Treated Branch | Placebo Branch | M Branch | Waste |
|---|---|---|---|---|---|
| Q | 1 | 5 | 0 | 10 | 15 |
|   | 2 | 1 | 1 | 21 | 7 |
|   | 3 | 0 | 4 | 16 | 10 |
|   | 4 | 5 | 2 | 14 | 9 |
|   | 5 | 1 | 1 | 22 | 6 |
|   | 6 | 2 | 0 | 19 | 9 |
| Mean | | 2.333333333 | 1.333333333 | 17 | 9.33333333 |
| Median | | 1.5 | 1 | 17.5 | 9 |
| Standard deviation | | 2.160246899 | 1.505545305 | 4.5607017 | 3.14112506 |

Test Treated–placebo p = 0.625

TABLE 5

Kairomone R

| Replica | | Treated Branch | Placebo Branch | M Branch | Waste |
|---|---|---|---|---|---|
| R | 1 | 2 | 2 | 20 | 6 |
|   | 2 | 2 | 2 | 22 | 4 |
|   | 3 | 1 | 1 | 22 | 6 |
|   | 4 | 0 | 3 | 16 | 11 |
|   | 5 | 0 | 0 | 22 | 8 |
|   | 6 | 3 | 3 | 12 | 12 |
| Mean | | 1.333333333 | 1.833333333 | 19 | 7.83333333 |
| Median | | 1.5 | 2 | 21 | 7 |
| Standard deviation | | 1.211060142 | 1.169045194 | 4.14728827 | 3.12516666 |

Test Treated–placebo p = 1

TABLE 6

Kairomone S

| Replica | | Treated Branch | Placebo Branch | M Branch | Waste |
|---|---|---|---|---|---|
| S | 1 | 3 | 4 | 11 | 12 |
|   | 2 | 5 | 0 | 11 | 14 |
|   | 3 | 0 | 6 | 13 | 11 |
|   | 4 | 7 | 0 | 8 | 15 |

TABLE 6-continued

Kairomone S

| Replica | | Treated Branch | Placebo Branch | M Branch | Waste |
|---|---|---|---|---|---|
|   | 5 | 4 | 1 | 16 | 9 |
|   | 6 | 1 | 2 | 22 | 5 |
|   | 7 | 0 | 2 | 14 | 14 |
|   | 8 | 0 | 0 | 19 | 11 |
|   | 9 | 1 | 1 | 24 | 4 |
|   | 10 | 5 | 0 | 15 | 10 |
| Mean | | 2.6 | 1.6 | 15.3 | 10.5 |
| Median | | 2 | 1 | 14.5 | 11 |
| Standard deviation | | 2.547329757 | 2.011080417 | 5.07827617 | 3.68932394 |

Test Treated–placebo p = 0.516

Between all the mixtures used in this trial, the only one which provided really interesting results was A. This solution may be regarded as a putative allomone mixture. To the contrary, the tests with E lead to some contradictory results, the product giving no significant attracting effect. The contradiction with the previous test may be the consequence for the lack of precision in the Smiley Chamber system.

Example 4—Evaluation of the Putative Semiochemicals in an Infestation Test

Taking in account the results of the previous tests, the focus was on the putative semiochemicals A, B, E, F and P, which were positively selected or not tested during the previous tests set forth in Examples 1 to 3. Based on the results the identification of the specific signal which lead the copepodits to detach will tried to be identified.

The following are the compounds set forth in the semiochemicals A, B, E, F and P:
- A: containing 30% palmitoleic acid, 20% aldehyde C13tridecanal and 50% oleyl alcohol.
- B: containing 50% palmitoleic acid and 50% squalene.
- E: containing 30% palmitoleic acid, 30% oleic acid and 40% squalene.
- F: containing 50% squalene, 30% aldehydeC13 tridecanal and 30% oleic acid.
- P: containing 17% myristic acid, 17% palmitic acid, 56% palmitoleic acid and 10% oleic acid.

Figure 6:
FIG. 6 is a photograph of the beginning of the Infestation test. The smolts are placed in the tanks where they are kept in 3 ppm of either the semiochemical product comprising a synthesized palmitoleic acid or placebo.

This test exposed young salmons (smolts weighting almost 70 grams) to a high density group of copepodits during 45 minutes in a testing device, which consisted of four 23 cm diameter tanks, with an outflow. The testing device was protected by a tent, which did not allow any shadow or uncontrolled light around the fish. Light can modify the behavior of the copepodits which have phototropism. Each tank received a smolt for 45 min (FIG. 6).

The copepodits were first fished out of their rearing tank and counted on a stereomicroscope. Four infesting doses of copepodits, containing 60 copepodits each, were prepared for each run of the test. The smolts were placed in a tank containing the treatment solution (or the placebo), which concentration in active substance was 6 ppm. This bath lasted for 10 minutes.

Then the smolts were placed in a tank where they were kept in 3 ppm of the same treatment (product or placebo) used in the previous bath to begin the testing. The purpose of this process was to prevent any dramatic decrease in the concentration of the active product on their skin.

During the first 10 minutes, the outflow was open and the tent was closed. At that moment each tank was refilled to reach the initial volume of oxygenated liquid (refilled with the same solution, product or placebo). The outflow was then closed for 5 minutes and the infesting dose was introduced in the tank. Then the outflow was opened and stayed opened for 30 minutes with a refill every 10 minutes (without opening the tent).

After 45 minutes of exposure to the copepodits, the smolts were euthanized by administration of a toxic dose of anaesthetic agent Benzoake, at a concentration of 10 times the normal dose of 30 to 40 mg/l.

Figure 7:
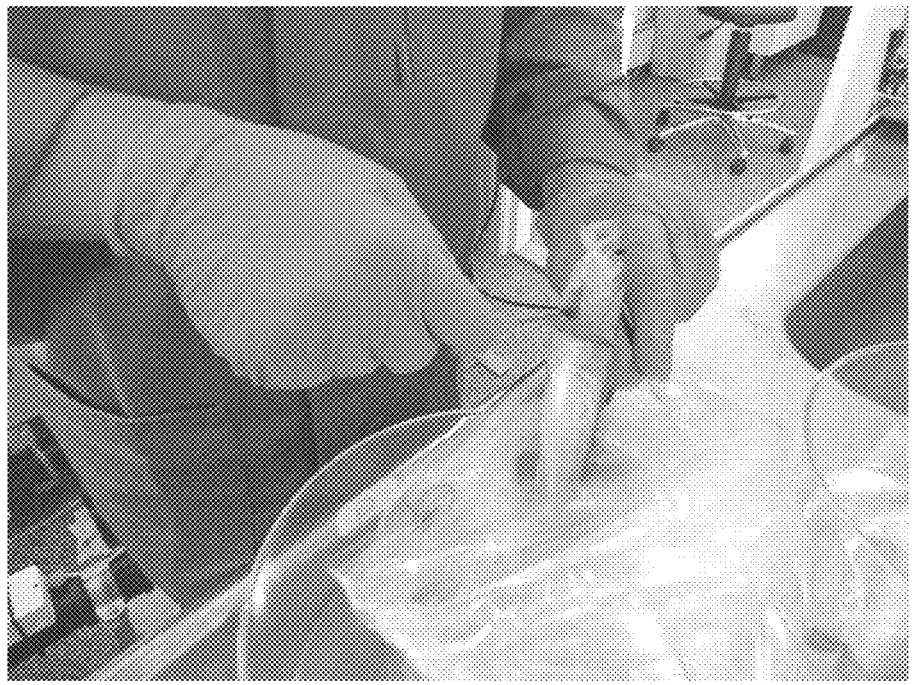
FIG. 7 is a photograph showing the harvest of copepodits by rubbing the fish with a metallic spoon to remove all the possible copepodits attached to the fish.

The dead fish were placed in a plastic bag in which they were rubbed and rinsed with sea water. The skin of the fish was rubbed with a metallic spoon, to remove all the possible copepodits attached on it, as shown in FIG. 7.

Each fish was washed thus detaching all of the copepodits and shells from the fish skin. The collected liquid from the washing was filtered to count the parasites. The copepodits were counted on the filter to obtain the number of copepodites on the outer body of the fish. The gills were then dissected to count the number of copepodits on the gills.

The first phase of the test compared the number of copepodits on the body and on the gills, between replicas of the test. The purpose of this phase was to validate the test and measure its standard deviation.

The second phase of the test compared the number of copepodits (abbreviated cops in the Tables below) on the body and on the gills, between treated smolts and reference smolts, as a control, which were just bathed in seawater plus ethyl alcohol for the five solutions. The results are shown in the tables below.

TABLE 7

| Reference/Control | | |
|---|---|---|
| Replicas | Cop on body | Cop on gills |
| 1 | 21 | 1 |
| 2 | 21 | 1 |
| 3 | 18 | 5 |
| 4 | 18 | 2 |
| 5 | 23 | 3 |
| 6 | 18 | 1 |
| 7 | 18 | 5 |
| 8 | 24 | 2 |
| 9 | 21 | 5 |
| 10 | 30 | 5 |
| mean | 21.2 | 3.0 |
| Standard deviation | 3.8 | 1.8 |

TABLE 8

| Semiochemical A | | |
|---|---|---|
| Replicas | Cop on body | Cop on gills |
| 1 | 21 | 0 |
| 2 | 15 | 2 |
| 3 | 17 | 2 |
| 4 | 15 | 1 |
| 5 | 12 | 4 |
| 6 | 18 | 1 |
| 7 | 22 | 1 |
| mean | 17.1 | 1.6 |
| Standard deviation | 3.5 | 1.3 |

TABLE 9

| Semiochemical B | | |
|---|---|---|
| Replicas | Cop on body | Cop on gills |
| 1 | 23 | 3 |
| 2 | 24 | 1 |
| 3 | 17 | 0 |
| 4 | 25 | 3 |
| 5 | 25 | 1 |
| 6 | 13 | 7 |
| mean | 21.2 | 2.5 |
| Standard deviation | 5.0 | 2.5 |

TABLE 10

| Semiochemical E | | |
|---|---|---|
| Replicas | Cop on body | Cop on gills |
| 1 | 25 | 3 |
| 2 | 17 | 1 |
| 3 | 18 | 5 |
| 4 | 15 | 4 |
| 5 | 5 | 2 |
| 6 | 22 | 2 |
| 7 | 7 | 6 |
| 8 | 15 | 1 |
| mean | 15.5 | 3.0 |
| Standard deviation | 6.8 | 1.9 |

TABLE 11

| Semiochemical F | | |
|---|---|---|
| Replicas | Cop on body | Cop on gills |
| 1 | 23 | 4 |
| 2 | 30 | 4 |
| 3 | 15 | 4 |
| 4 | 25 | 4 |
| mean | 23.3 | 4.0 |
| Standard deviation | 6.2 | 0.0 |

TABLE 12

| Semiochemical P | | |
|---|---|---|
| Replicas | Cop on body | Cop on gills |
| 1 | 23 | 6 |
| 2 | 21 | 6 |
| 3 | 21 | 5 |
| 4 | 21 | 5 |
| mean | 21.5 | 5.5 |
| Standard deviation | 1.0 | 0.6 |

The reproducibility of this test appeared to be very interesting with somehow constant number of copepodits on the body of the fish. According to the literature (Tully et al 2002), this kind of infestation is low and very probably related to a very high concentration of copepodits in this test.

These data do not provide any significant effect for any of the tested solutions. Looking at the results obtained with A, as described above, it appeared that this solution does not show the same effect in this test compared with the previous tests. A, as described above, is not capable of inhibiting the attachment of copepodits on smolts. Notwithstanding the lack of significance, the number of body copepodits, in the smolts treated with A, as described above, looks somehow lower compared to the reference or to the other putative allomones. Interestingly, all those putative mixtures contain one common compound, palmitoleic acid.

Example 5—Repeat of Example 4 with Palmitoleic Acid

The same test as in Example 4 was repeated using palmitoleic acid. The results are shown in Table 13 below.

TABLE 13

| | Palmitoleic Acid | |
|---|---|---|
| Replicas | Cop on body | Cop on gills |
| 1 | 6 | 0 |
| 2 | 11 | 3 |
| 3 | 7 | 5 |
| 4 | 8 | 3 |
| mean | 8.0 | 2.8 |
| Standard deviation | 2.2 | 2.1 |

Palmitoleic acid provided an important reduction of the infestation.

This test, compared to Bron et al (1993) and Tully and al (2002) data, raised the question of a possible "body infestation" revealed by such experimental infestation. The copepodits tend to attach to moving bodies affected by sudden accelerations (Heuch and Karlsen 1997). In this example, a high density population of copepodits was continuously around the fish. It makes sense to suspect that, even in presence of effective allomones, it leads to multiple successions of attachment-detachment for the copepodits. Thus, when the test was finished, there was always some copepodits recently attached on the body, which have not had time to detach when harvested on the dead fish. Such a hypothesis exposes any attempt to validate a possible allomonal product, to the risk of false negative results.

Example 6—Validation of Allomone Palmitoleic Acid

The best way to confirm the hypothesis that the copepodits did not have time to detach prior to being harvested on the dead fish was to run the same test in a three branch protocol: the two same branches as in the previous protocol (reference and treatment branches) plus a new branch including a negative reference by using fish which species is not naturally a host to *Lepeophtheirus*.

In this example, synthesized palmitoleic acid was tested following the very same protocol but with 3 groups of fishes: (1) Positive reference: smolts without treatment; (2) Negative reference: juvenile cods (*Gadus morhua*) comparable in size; and (3) Treatment group: smolts receiving palmitoleic acid.

The same experiment was undertaken as described in Example 4. The results are set forth in Tables 14 and 15 below:

TABLE 14

| Number of copepodits attached to body | | |
|---|---|---|
| Control salmons | Treated salmons | Control cods |
| 21 | 4 | 7 |
| 21 | 3 | 8 |
| 20 | 5 | 4 |
| 17 | 8 | 2 |
| 21 | 7 | 6 |
| 21 | 11 | 3 |

TABLE 14-continued

| Number of copepodits attached to body | | |
|---|---|---|
| Control salmons | Treated salmons | Control cods |
| 18 | 5 | 3 |
| 18 | 9 | |
| 23 | 5 | |
| 18 | 10 | |
| 18 | 6 | |
| 24 | 5 | |
| 21 | 6 | |
| 30 | 1 | |
| | 7 | |
| | 8 | |
| Mean 20.78571429 | 6.25 | 4.714285714 |
| Standard-error 3.35533035 | 2.594866727 | 2.288688541 |
| S.E.M 0.896749756 | 0.648716682 | 0.865042958 |
| Median 21 | 6 | 4 |
| β risk(Control salmons/Treated salmons) | | 0.00% |
| β risk (Control salmons/Control cods) | | 0.00% |
| β risk (Treated salmons/Control cods) | | 71.52% |

TABLE 15

| Number of copepodits attached in the gills | | |
|---|---|---|
| Control salmons | Treated salmons | Control cods |
| 0 | 0 | 2 |
| 4 | 0 | 2 |
| 7 | 0 | 0 |
| 5 | 0 | 1 |
| 1 | 2 | 0 |
| 1 | 3 | 0 |
| 5 | 5 | 0 |
| 2 | 1 | |
| 3 | 8 | |
| 1 | 3 | |
| 5 | 4 | |
| 2 | 1 | |
| 5 | 0 | |
| 5 | 3 | |
| | 5 | |
| | 3 | |
| Mean 3.285714286 | 2.375 | 0.714285714 |
| Standard-error 2.127785827 | 2.334523506 | 0.951189731 |
| S.E.M 0.568674683 | 0.583630876 | 0.359515925 |
| Median 3.5 | 2.5 | 0 |
| B risk (Control salmons/Treated salmons) | | 79.95% |
| β risk (Control salmons/Control cods) | | 7.59% |
| β risk (Treated salmons/Control cods) | | 45.57% |

Figure 8:
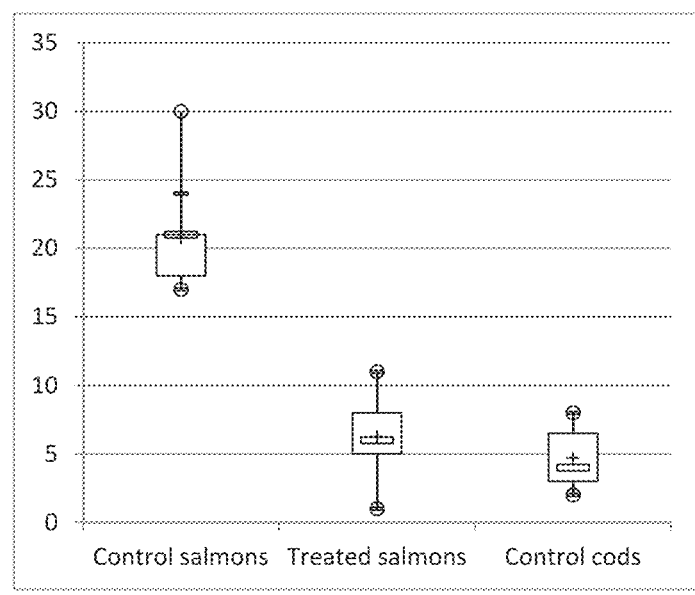
FIG. 8 are box plot graphs showing the results of Example 6 of the control salmons and control cods versus the treated salmons.
Figure 8:
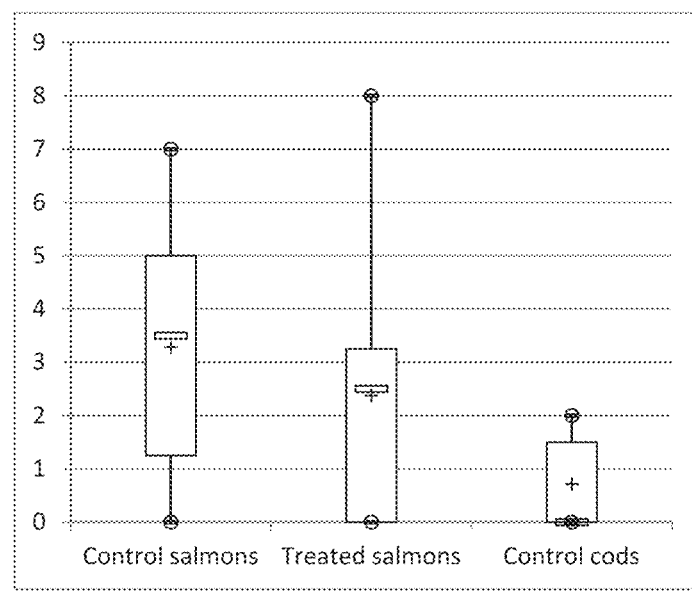
Figure 9:
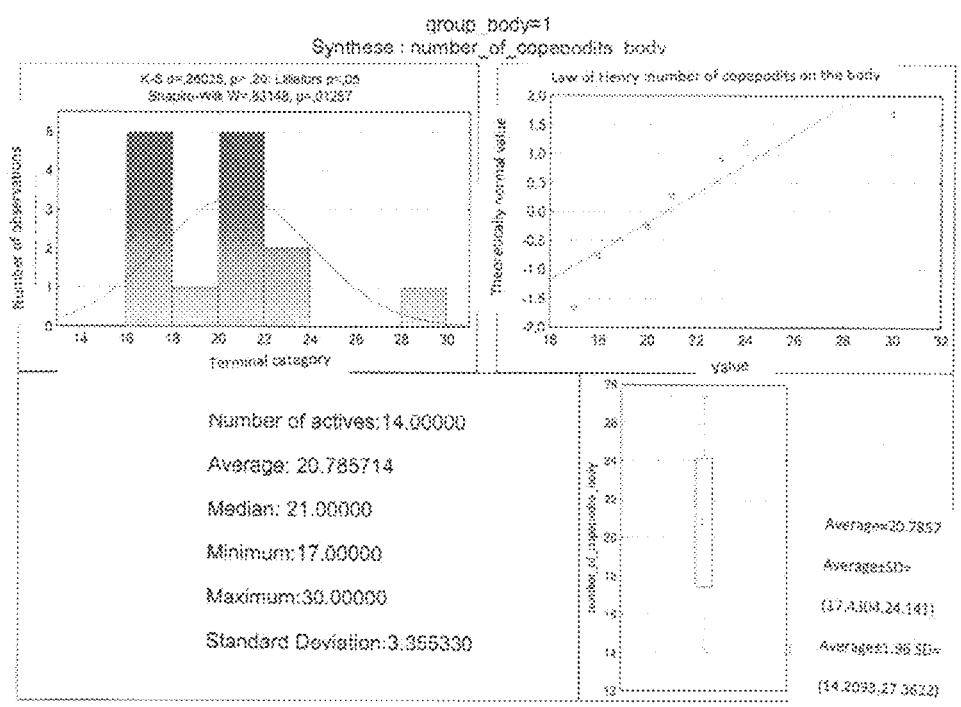
FIG. 9 is graph showing the number of copepodits in the control group of Example 6.
Figure 10:
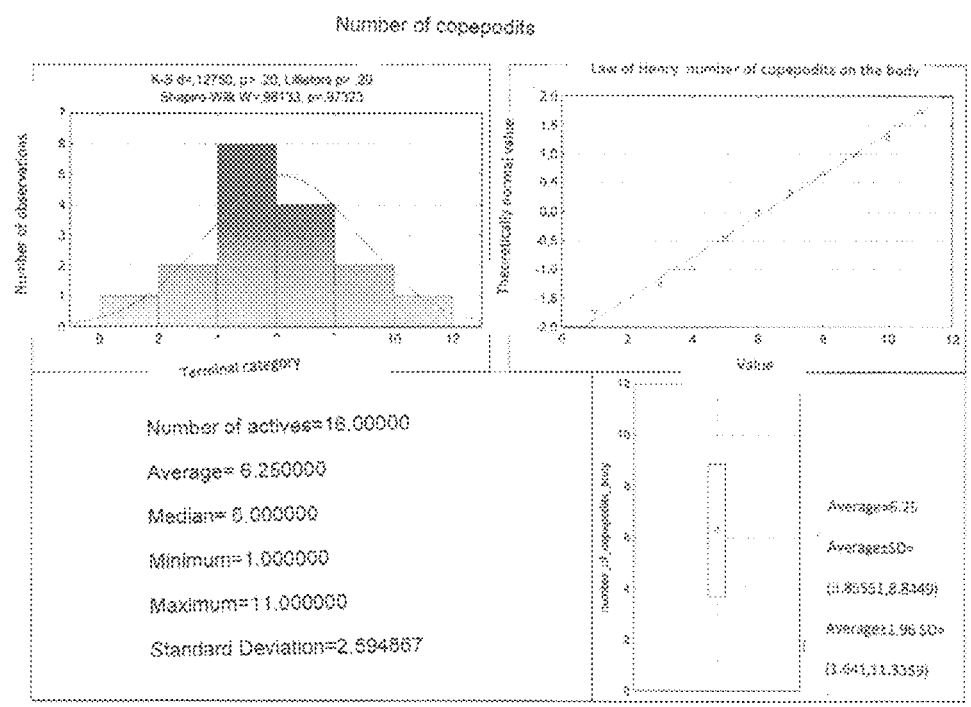
FIG. 10 is graph showing the number of copepodits in the tested salmon group of Example 6.
Figure 11:
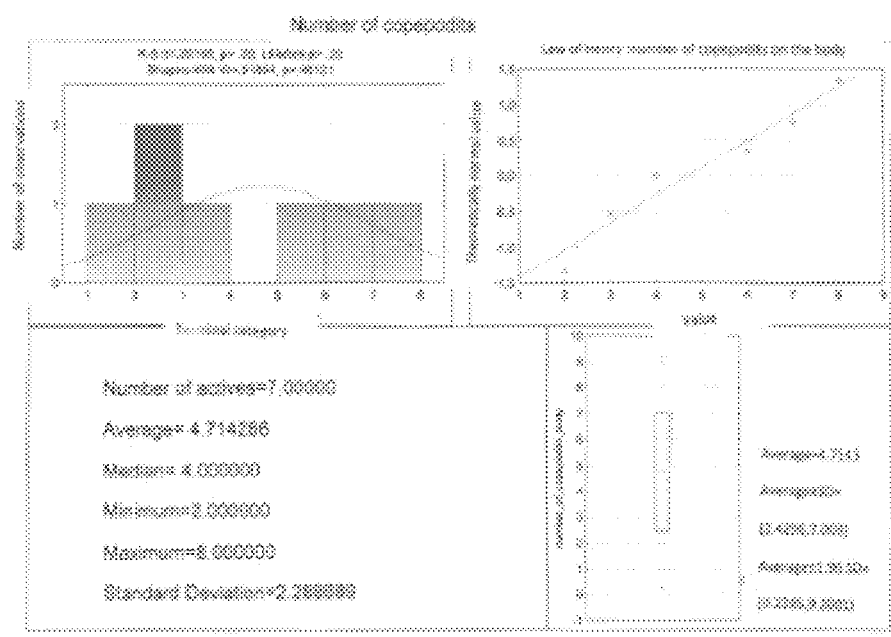
FIG. 11 is graph showing the number of copepodits in the control cod group of Example 6.

The box plot results are shown in FIG. 8. Statistical analysis of the results was undertaken and shown in FIGS. 9 to 11. A Levene's test was undertaken, which is an inferential statistic to assess the equality of variances for a variable calculated for two or more groups. The results are shown in Table 16 below.

TABLE 16

| Levene Test Variance Homogeneity Effect of "group body" Ddl for F: 2.34 | | | |
|---|---|---|---|
| | MC Effect | MC risk | F | p |
| Number of copepodits-body | 0.254139 | 3.392569 | 0.074910 | 0.927979 |

The distribution was normal for the 3 groups.

A Tukey's HSD test was undertaken and the results are shown in Table 17 below.

TABLE 17

Tukey HSD Test
Number of copepodits per body
Approach Probabilities for Post Hoc Tests
Risk: MC Inter = 8.1996, dl = 34.000

| Cell N° | Group-body | 1<br>20.786 | 2<br>6.2500 | 3<br>4.7143 |
|---|---|---|---|---|
| 1 | 1 |  | 0.000125 | 0.000125 |
| 2 | 2 | 0.000125 |  | 0.471026 |
| 3 | 3 | 0.000125 | 0.471026 |  |

These results showed highly significant differences between control salmons and control cods, and between control salmons and treated salmons, but no significant difference between treated salmons and control cods.

Discussion and Conclusion:

The hypothesis of a "passive body infestation" in Examples 4 to 6 was confirmed. There are copepodits attaching on the cods, which is a fish that is not naturally a host to *Lepeophtheirus salmonis*. The infestation on gills, was also a passive infestation mostly related to high density of copepodits in experimental infestation.

The allomone palmitoleic acid induces a highly significant reduction in the number of copepodits attached on the body of the salmon. Synthesized palmitoleic acid treated salmons are infested in a comparable way to cods, a naturally non infested species for *Lepeophtheirus salmonis*.

Example 7—Efficacy of an Isomer of Sea Lice Copepodites Attachment Inhibiting Semiochemical as an Inhibitor of Infestation Behavior of *Lepeophtheirus Salmonis* Copepodids in Atlantic Salmon (*Salmo Salar*)

The aim of this example was to test the efficacy of an isomer of Sea Lice Copepodids Attachment Inhibiting Semiochemical (SCAIS) as an inhibitor of the infestation behavior of *Lepoephtheirus salmonis* copepodids in Atlantic salmon (*Salmon salar*).

This isomer of Sea Lice Copepodits Attachment Inhibiting Semiochemical (SCAIS) that was used in this example was trans-9-hexadecenoic acid.

The test was realized using 4 rounds of 4 fish, eight of which were treated with trans-9-hexadecenoic acid and the other eight used as a control. For each round 4 fish were tested; i.e., 2 treated fish and 2 controls.

To be included in the study the smolts had to have a body weight between 70 g and 150 g and the copepodits had to be able to swim actively. If the smolts had disease, loss of scales, fin damage, cataracts and/or swam abnormally they were not used in the study. If the copepodits were immobile after stimulation, they were rejected from the study.

For each round 4 fish are caught and introduced into four 2-liter flat beakers supplied with 1.75 liters of seawater. The treated fish had 6 ppm of trans-9-hexadecenoic acid placed in their seawater, while in the control only seawater was used. 0.52 ml of the treatment or control were directly injected into 1.75 liters of seawater. The 4 fish were bathed in this solution for 10 minutes.

The fish were then transferred to another 3.5 liter beaker supplied with 3.5 liters of seawater treated either with 3 ppm of trans-9-hexadecenoic acid or a control of simply seawater. 0.52 ml of the treatment of control were directly injected into 3.5 liters of seawater. The flat beakers were equipped with a valve such that 0.875 liters were emptied from the flat beaker. When the fish were introduced into the beakers, the valves were turned on. Ten minutes after the valves were turned on, the beakers were supplied with either 0.875 liters of the treatment of trans-9-hexadecenoic acid or 0.875 liters of the control of seawater. Ten minutes thereafter (20 minutes after the introduction of the fish into the beakers), the valves were turned off and 60 copepodits per fish were injected into each flat beaker. Five minutes later (25 minutes after introduction of the fish into the beakers), the valves were turned on. Ten minutes later (35 minutes after introduction of the fish into the beakers) each beaker was supplied with either 0.875 liters of trans-9-hexadecenoic acid or 0.875 liters of the control of seawater. Ten minutes later (45 minutes after introduction of the fish into the beakers) each beaker was supplied with either 0.875 liters of trans-9-hexadecenoic acid or 0.875 liters of the control of seawater. Ten minutes later (55 minutes after introduction of the fish into the beakers) each beaker was supplied with either 0.875 liters of trans-9-hexadecenoic acid or 0.875 liters of the control of seawater.

2 ml of Benzoak® was then injected into each flat beaker in order to kill the fish by an overdose of an anesthetic product. The fish were then introduced into a plastic bag, which was coded. The fish were held using surgical pliers in the gills chamber and scrubbed three times at different places on the fish. The top of the fish was first scrubbed, then rinsed in the plastic bag, the bottom of the fish was next scrubbed, then rinsed in the plastic bag and then the entire fish was scrubbed and rinsed in the plastic bag. The fish were then removed from the plastic bag and weighed. The content of plastic bag was then emptied above a filter and the number of copepodits was then counted on each filter using a magnifying glass. This process was repeated for the other fish and other rounds of fish.

Table 18 is illustrative of the rounds of fish tested and whether they were treated with trans-9-hexadecenoic acid or the control of seawater.

TABLE 18

| Round | Left | Central Left | Central Right | Right |
|---|---|---|---|---|
| 1 | SCAIS$^{iso}$ | SCAIS$^{iso}$ | Control | Control |
| 2 | Control | SCAIS$^{iso}$ | SCAIS$^{iso}$ | Control |
| 3 | Control | Control | SCAIS$^{iso}$ | SCAIS$^{iso}$ |
| 4 | SCAIS$^{iso}$ | Control | Control | SCAIS$^{iso}$ |

Where SCAIS$^{iso}$ in Table 18 refers to trans-9-hexadecenoic acid.

Table 19 are the results obtained from this example.

TABLE 19

| Code | treatment | Number of copepodits | Body mass |
|---|---|---|---|
| 1L | SCAIS$^{iso}$ | 9 | 94 |
| 1CL | SCAIS$^{iso}$ | 10 | 105 |
| 1CR | control | 19 | 122 |
| 1R | control | 20 | 86 |
| 2L | control | 18 | 97 |
| 2CL | SCAIS$^{iso}$ | 8 | 77 |
| 2CR | SCAIS$^{iso}$ | 4 | 89 |
| 2R | control | 15 | 92 |
| 3L | control | 20 | 115 |
| 3CL | control | 19 | 77 |
| 3CR | SCAIS$^{iso}$ | 16 | 84 |

TABLE 19-continued

| Code | treatment | Number of copepodits | Body mass |
|---|---|---|---|
| 3R | SCAIS$^{iso}$ | 16 | 100 |
| 4L | SCAIS$^{iso}$ | 9 | 92 |
| 4CL | control | 21 | 80 |
| 4CR | control | 17 | 101 |
| 4R | SCAIS$^{iso}$ | 8 | 84 |

Where SCAIS$^{iso}$ in Table 19 refers to trans-9-hexadecenoic acid.

In the case of exclusion criteria or a defective trial, the experiment was repeated with reserve fish until 8 treated and 8 controls were obtained. Outliers (atypical values) were removed from the data if qualified as absurd results. If the centering and reduction of the data is superior to 3 in absolute value it was considered to be an outlier. No atypical values were found in this study.

Data was analyzed using 9.4 SAS software (2002-2012 by SAS Institute Inc., Cary, N.C., U.S.A.). All data was tested for evidence of departures from the assumption of normality using residual diagnostics plots using the univariate procedure in SAS 9.4 software. The comparison between control and treated groups according to body mass and number of attached copepodids was carried out using a Student t test using the t test procedure or the Wilcoxon Two-Sample Test using the npar1 way procedure in SAS 9.4 software depending on the normality and variances. The homogeneity of the variances were verified using the Fisher test using the t test procedure. The significance threshold was conventionally set at 5%.

TABLE 20

| treatment | N Obs | Variable | N | N Miss | Mean | Std Dev | Std Error | Median | Lower Quartile | Upper Quartile |
|---|---|---|---|---|---|---|---|---|---|---|
| control | 8 | Nb copepodits | 8 | 0 | 18.6250000 | 1.9226098 | 0.6797452 | 19.0000000 | 17.5000000 | 20.0000000 |
|  |  | body mass | 8 | 0 | 96.2500000 | 16.0156174 | 5.6623758 | 94.5000000 | 83.0000000 | 108.0000000 |
| SCAIS$^{iso}$ | 8 | Nb copepodits | 8 | 0 | 10.0000000 | 4.1057451 | 1.4516001 | 9.0000000 | 8.0000000 | 13.0000000 |
|  |  | body mass | 8 | 0 | 90.6250000 | 9.1329466 | 3.2289842 | 90.5000000 | 84.0000000 | 97.0000000 |

Where SCAIS$^{iso}$ in Table 20 refers to trans-9-hexadecenoic acid and Nb refers to the number.

The tests for normality were undertaken and the results are set forth in Table 21 below for trans-9-hexadecenoic acid.

TABLE 21

| Tests for Normality | | | | |
|---|---|---|---|---|
| Test | | Statistic | | p Value |
| Shapiro-Wilk | W | 0.980201 | Pr < W | 0.9639 |
| Kolmogorov-Smirnov | D | 0.140895 | Pr > D | >0.1500 |
| Cramer-von Mises | W-Sq | 0.021976 | Pr > W-Sq | >0.2500 |
| Anderson-Darling | A-Sq | 0.154445 | Pr > A-Sq | >0.2500 |

The tests for normality were undertaken and the results are set forth in Table 22 below for the control.

TABLE 22

| Tests for Normality | | | | |
|---|---|---|---|---|
| Test | | Statistic | | p Value |
| Shapiro-Wilk | W | 0.945725 | Pr < W | 0.6681 |
| Kolmogorov-Smirnov | D | 0.133391 | Pr > D | >0.1500 |
| Cramer-von Mises | W-Sq | 0.030068 | Pr > W-Sq | >0.2500 |
| Anderson-Darling | A-Sq | 0.21824 | Pr > A-Sq | >0.2500 |

All the tests used concluded the normality of body mass for the fish tested for the trans-9-hexadecenoic acid and the control.

The results from the Fisher's test for homogeneity of variances are set forth in Table 23 below.

TABLE 23

| Equality of Variances | | | | |
|---|---|---|---|---|
| Method | Num DF | Den DF | F Value | Pr > F |
| Folded F | 7 | 7 | 3.08 | 0.1615 |

Variances between treatment groups were homogeneous for "Body mass"

The of Student's t-test was used and the results are shown in Table 24 below.

TABLE 24

| Method | Variances | DF | t Value | Pr > |t| |
|---|---|---|---|---|
| Pooled | Equal | 14 | 0.86 | 0.4027 |
| Satterthwaite | Unequal | 11.117 | 0.86 | 0.4064 |

Salmons were homogeneous between treatment groups according to "body mass". (p=0.4027)

CONCLUSION

Atlantic salmons are homogeneous between treatment groups for "body mass." Trans-9-hexadecenoic acid (SCAIS$^{iso}$) has a significant effect on the number of copepodits attached in Atlantic salmons with a lower number of attached copepodits in trans-9-hexadecenoic acid (SCAIS$^{ISO}$) treated salmons.

Example 8—Fabrication of the Sea Lice Copepodits Attachment Inhibiting Semiochemical Tablet Water dispersible tablets containing the sea lice copepodites attachment inhibiting semiochemical are fabricated as follows. 13.2 g of the sea lice copepodites attachment inhibiting semiochemical are blended with 150 g Eudragit RL, 200 g of ethyl acetate and 110 g of microcrystalline cellulose. 2.5% magnesium stearate and 5% talc is blended together and added to the initial formulation containing the semiochemical. The mixture is compressed using a station rotary tableting machine with a flat punch of 8 mm diameter.

Example 9—Efficacy of the Sea Lice Copepodits Attachment Inhibiting Semiochemical The purpose of this example was to assess the efficacy of the sea lice copepodits attachment inhibiting semiochemical (SCAIS), continuously released by water dispersible tablets, on the infestation behaviour of Lepeophtheirus salmonis copepodids in Atlantic salmon smolts (Salmo salar).

The sea lice copepodites attachment inhibiting semiochemical (SCAIS) used in this example was cis-9-hexadecenoic acid (palmitoleic acid).

72 Atlantic salmon (Salmo salar) in the smolt stage having a weight around 90 g and of the origin SALMAR® (Daugstad 6392 Vikebukt, Norway) were used in this study. 2,400 copepodits used were from the species Lepeophtheirus salmonis origin Ilab® (Bergen, Norway).

To be included in the study the smolts had to have a body weight between 70 g and 150 g and the copepodits had to be able to swim actively. If the smolts had disease, loss of scales, fin damage, cataracts and/or swam abnormally they were not used in the study. If the copepodits were immobile after stimulation, they were rejected from the study.

If during the experiment the smolts swam on their backs, they were excluded from the data in the study.

Infestation tests were measured at 1 hour, 24 hours, 72 hours and 120 hours after application of the treatment. Blood tests were undertaken at 0 hours, 1 hour, 24 hours, 72 hours and 120 hours after treatment.

40 fish per tank were used and the study was conducted in two parallel groups of Atlantic salmon smolts, one group was treated with the sea lice copepodits attachment inhibiting semiochemical tablets of cis-9-hexdecenoic acid, which were placed in a string bag half way down where the water resides in the rearing tank and the other group was the control using only ethyl alcohol.

To obtain the blood samples 4 fish were caught in each of the two tanks and introduced in an anesthetic bath of 0.7 ml/l of Benzoak®. After 1 minute a blood sample was collected in the caudal vein of the fish using a 2.5 ml syringe with a 0.6 mm needle. A drop of blood was placed on a glass slide and a blood smear was performed using a plastic strip. The ratio of heterophils and lymphocytes (H/L) was measured from these blood smears using a Diff-Quick stain, which is a stain that is a modification of the Wright-Giemsa stain. The rest of the blood was injected into a 4 ml heparinized tube and was stored in a freezer at −18° C. until subsequent analysis of plasma cortisol. The total plasma cortisol test was analyzed via an ELISA test kit from the blood samples at a 1:25 dilution ($ng \cdot ml^{-1}$).

The infestation test, carried out at 1 hour, 24 hours, 72 hours and 120 hours after application of the treatment was performed in the following manner. Two fish were caught in each of the two tanks (control and test) and were introduced into four 3.5 liter flat beakers supplied with 3.5 liters of water sampled from the original tank of each fish. The flat beakers were equipped with valves that enable to empty 0.875 liters of solution when the equivalent amount of solution was introduced into the beakers. When the fish were introduced into the beakers the valves were turned on. Ten minutes after introduction of the fish, the flat beakers were supplied with 0.875 liters of their respective solution (test or control). Ten minutes after (20 minutes after introduction of the fish into the flat beakers the valves were turned off. 60 copepodits per fish were injected into each flat beaker. Five minutes after injection of the copepodits (25 minutes after introduction of the fish into the flat beaker) the valves were turned on. Ten minutes later (35 minutes after introduction of the fish into the flat beaker) each flat beaker was supplied with its respective treatment of cis-9-hexdecenoic acid or control. Ten minutes after (45 minutes after introduction of the fish into the flat beaker) each flat beaker was supplied with its respective treatment of cis-9-hexdecenoic acid or control. Ten minutes after (55 minutes after introduction of the fish into the flat beaker) each flat beaker was supplied with its respective treatment of cis-9-hexdecenoic acid or control. Ten minutes after (65 minutes after introduction of the fish into the flat beaker) 2 ml of Benzoak® was injected into each flat beaker to kill the fish via an overdose of anesthetic product. When the fish were dead they were introduced individually into a plastic bag.

Each fish was held in the plastic bag using surgical pliers, which were introduced into the gills chamber of the fish. The fish was then scrubbed three times in the plastic bag; i.e., the top of the fish was scrubbed and was rinsed with water, the bottom of the fish was scrubbed and rinsed with water and the entire fish was scrubbed and rinsed with water. The fish was then removed from the bag and weighed. The water content of the plastic bag was then emptied over a filter to collect the copepodits. A magnifying glass was used to count the number of copepodits on each filter.

This process was repeated for the other seven rounds of fish.

In the case of exclusion criteria or a defective trial, the experiment was repeated with reserve fish. To manage missing data and outliers, this type of data was not included in the overall results.

The preliminary analysis showed a positive tendency in favor of the treated group. The mean number of copepodits attached to the control smolts was 15.4, while the mean number attached to the treatment group was 10.6. These results indicate that sea lice copepodits attachment inhibiting semiochemicals of cis-9-hexadecenoic acid binds quickly and effectively to the mucus of the fish providing a significant protection in infestation tests of high severity of 60 copepodits per fish in a closed 3.5 liter tank.

Palmitoleic acid (cis-9-hexdecenoic acid) and the isomer of trans-9-hexadecenoic acid may be regarded as the SCAIS (Sealice Copepodites Attachment Inhibiting Semiochemical), responsible for the selection of acceptable host for the salmon lice. Palmitoleic acid, a low molecular weight chemical compound, observed as a metabolic product in many species, and known for its non-toxicity, is a promising option for the prevention of sea lice infestation in salmonid fish farming.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. A composition comprising from about 0.1 ppm to about 10 ppm of a synthesized palmitoleic acid, salts thereof, isomers thereof and/or structural analogs that maintain their semiochemical capabilities thereof that detach sea lice from fish and/or mixtures thereof and an acceptable vehicle, wherein said isomers are selected from the group consisting of 11-cis-hexadecenoic acid, 9-cis,12-cis hexadecanoic acid and trans-9-hexedecenoic acid and wherein said structural analogs are selected from the group consisting of 2-methoxy-5-hexadecenoic acid, ω-fluoropalmitoleic acid, nitrated palmitoleic acid, chlorinated palmitoleic acid and ω-hydroxydecenoic acid, and wherein said composition is a sea lice copepodites attachment inhibiting semiochemical composition.

2. The composition according to claim 1, comprising from about 0.6 ppm to about 6 ppm of a synthesized palmitoleic acid, salts thereof, isomers thereof and/or structural analogs that maintain their semiochemical capabilities to detach sea lice from fish and/or mixtures thereof and an acceptable vehicle.

3. The composition according to claim 1, further comprising a nontoxic filler and/or enhancer composition.

4. The composition according to claim 3, wherein said nontoxic filler is selected from the group of fatty acids, alcohols, amines, squalene, glycerol and mixtures thereof.

5. The composition according to claim 3, wherein the enhancer composition contains amines and fatty acids from indolic derivatives, esters of these amines and fatty acids, ketones, acetone, alcohols or sterols.

6. The composition according to claim 1, wherein the acceptable vehicle is a pharmaceutically acceptable vehicle or a veterinarian acceptable vehicle.

7. The composition according to claim 1, wherein said composition can be in the form of powders, tablets, pellets, capsules, granulated, granular particles, dry flakes, in the form of a sustained release formulation, placed in micelles, liposomes, nanoparticles, microparticles, microencapsulated or lyophilzed.

8. A solution containing the composition according to claim 1.

9. The solution according to claim 8, formulated as a spray, an aerosol, an emulsion, a suspension, drops, in an underwater diffuser or in a slow release matrix.

10. The solution according to claim 8, wherein said solution can be added to the water where the fish resides or placed in the food of the fish.

11. The solution according to claim 8, which is administered orally or via injection to the fish.

12. A method to detach sea lice from fish, said method comprising:
    administering to fish a composition comprising from about 0.1 ppm to about 10 ppm of a synthesized palmitoleic acid, salts thereof, isomers thereof and/or structural analogs thereof to detach sea lice from fish and/or mixtures thereof and an acceptable vehicle,
    wherein said isomers are selected from the group consisting of 11-cis-hexadecenoic acid, 9-cis,12-cis hexadecanoic acid and trans-9-hexedecenoic acid and wherein said structural analogs are selected from the group consisting of 2-methoxy-5-hexadecenoic acid, ω-fluoropalmitoleic acid, nitrated palmitoleic acid, chlorinated palmitoleic acid and ω-hydroxydecenoic acid, and wherein said composition is a sea lice copepodites attachment inhibiting semiochemical composition.

13. The method according to claim 12, wherein said composition is administered at a concentration of about 0.6 ppm to about 6 ppm.

* * * * *